(12) United States Patent
van der Weide et al.

(10) Patent No.: US 11,596,474 B2
(45) Date of Patent: *Mar. 7, 2023

(54) ENERGY DELIVERY SYSTEMS AND USES THEREOF

(71) Applicant: NeuWave Medical, Inc., Madison, WI (US)

(72) Inventors: Daniel Warren van der Weide, Madison, WI (US); Fred T. Lee, Jr., Madison, WI (US); Paul F. Laeseke, Madison, WI (US); Christopher Lee Brace, Madison, WI (US)

(73) Assignee: NeuWave Medical, Inc., Madison, WI (US)

( * ) Notice: Subject to any disclaimer, the term of this patent is extended or adjusted under 35 U.S.C. 154(b) by 940 days.

This patent is subject to a terminal disclaimer.

(21) Appl. No.: 15/256,131

(22) Filed: Sep. 2, 2016

(65) Prior Publication Data

US 2016/0367318 A1 Dec. 22, 2016

Related U.S. Application Data

(63) Continuation of application No. 11/879,070, filed on Jul. 16, 2007.

(Continued)

(51) Int. Cl.
*A61B 18/18* (2006.01)
*A61B 90/00* (2016.01)
(Continued)

(52) U.S. Cl.
CPC .......... *A61B 18/1815* (2013.01); *A61B 18/18* (2013.01); *A61B 90/37* (2016.02);
(Continued)

(58) Field of Classification Search
CPC ................ A61B 18/18; A61B 18/1815; A61B 2018/1823; A61B 2018/183;
(Continued)

(56) References Cited

U.S. PATENT DOCUMENTS 3,800,552 A 4/1974 Sollami
3,838,242 A 9/1974 Goucher
(Continued)

FOREIGN PATENT DOCUMENTS

AU 2015/202149 5/2015
CN 2579361 10/2003
(Continued)

OTHER PUBLICATIONS

International Search Report & Written Opinion, International Patent Application No. PCT/US2017/027424, dated Oct. 9, 2017.
(Continued)

*Primary Examiner* — Jaymi E Della
(74) *Attorney, Agent, or Firm* — Casimir Jones, SC; Robert A. Goetz

(57) ABSTRACT

The present invention relates to comprehensive systems, devices and methods for delivering energy to tissue for a wide variety of applications, including medical procedures (e.g., tissue ablation, resection, cautery, vascular thrombosis, treatment of cardiac arrhythmias and dysrhythmias, electrosurgery, tissue harvest, etc.). In certain embodiments, systems, devices, and methods are provided for treating a tissue region (e.g., a tumor) through application of energy.

12 Claims, 13 Drawing Sheets

Related U.S. Application Data

(60) Provisional application No. 60/831,056, filed on Jul. 14, 2006, provisional application No. 60/853,911, filed on Oct. 24, 2006.

(51) Int. Cl.
  *A61B 17/00* (2006.01)
  *A61B 18/00* (2006.01)

(52) U.S. Cl.
  CPC .............. *A61B 2017/00274* (2013.01); *A61B 2018/00005* (2013.01); *A61B 2018/00023* (2013.01); *A61B 2018/0044* (2013.01); *A61B 2018/00351* (2013.01); *A61B 2018/00404* (2013.01); *A61B 2018/00446* (2013.01); *A61B 2018/00494* (2013.01); *A61B 2018/00511* (2013.01); *A61B 2018/00517* (2013.01); *A61B 2018/00529* (2013.01); *A61B 2018/00541* (2013.01); *A61B 2018/00547* (2013.01); *A61B 2018/00559* (2013.01); *A61B 2018/00577* (2013.01); *A61B 2018/00642* (2013.01); *A61B 2018/00702* (2013.01); *A61B 2018/00714* (2013.01); *A61B 2018/00791* (2013.01); *A61B 2018/00904* (2013.01); *A61B 2018/00982* (2013.01); *A61B 2018/1823* (2013.01); *A61B 2018/1861* (2013.01); *A61B 2090/374* (2016.02); *A61B 2090/376* (2016.02); *A61B 2090/378* (2016.02); *A61B 2090/3762* (2016.02)

(58) Field of Classification Search
  CPC .... A61B 2018/1838; A61B 2018/1846; A61B 2018/1853; A61B 2018/1861; A61B 2018/1869; A61B 2018/1876; A61B 2018/1884; A61B 2018/1892
  See application file for complete search history.

(56) References Cited

U.S. PATENT DOCUMENTS

| | | | |
|---|---|---|---|
| 3,991,770 A | 11/1976 | LeVeen | |
| 4,057,064 A | 11/1977 | Morrison | |
| 4,074,718 A | 2/1978 | Morrison | |
| 4,292,960 A * | 10/1981 | Paglione | A61B 18/18 600/2 |
| 4,312,364 A | 1/1982 | Convert | |
| 4,375,220 A | 3/1983 | Matvias | |
| 4,446,874 A | 5/1984 | Vaguine | |
| 4,494,539 A | 1/1985 | Zenitani | |
| 4,534,347 A | 8/1985 | Taylor | |
| 4,557,272 A | 12/1985 | Carr | |
| 4,586,491 A | 5/1986 | Carpenter | |
| 4,589,424 A | 5/1986 | Vaguine | |
| 4,601,296 A | 7/1986 | Yerushalmi et al. | |
| 4,621,642 A | 11/1986 | Chen | |
| 4,627,435 A | 12/1986 | Hoskin | |
| 4,641,649 A | 2/1987 | Walinsky | |
| 4,643,186 A | 2/1987 | Rosen | |
| 4,662,383 A | 5/1987 | Sogawa | |
| 4,700,716 A | 10/1987 | Kasevich | |
| 4,712,559 A | 12/1987 | Turner | |
| 4,776,086 A | 10/1988 | Kasevich | |
| 4,790,311 A | 12/1988 | Ruiz | |
| 4,800,899 A | 1/1989 | Elliott et al. | |
| 4,860,752 A | 8/1989 | Turner | |
| 4,880,015 A | 11/1989 | Nierman | |
| 4,901,719 A | 2/1990 | Trenconsky | |
| 4,945,912 A | 8/1990 | Langberg | |
| 4,974,587 A | 12/1990 | Turner et al. | |
| 5,007,437 A * | 4/1991 | Sterzer | A61B 18/18 604/915 |
| 5,026,959 A | 6/1991 | Ito | |
| 5,057,104 A | 10/1991 | Chess | |
| 5,057,106 A * | 10/1991 | Kasevich | A61B 18/18 600/549 |
| 5,074,861 A | 12/1991 | Schneider | |
| RE33,791 E | 1/1992 | Carr | |
| 5,098,429 A | 3/1992 | Sterzer | |
| 5,129,396 A | 7/1992 | Rosen | |
| 5,150,717 A | 9/1992 | Rosen | |
| 5,167,619 A | 12/1992 | Wuchinich | |
| 5,211,625 A | 5/1993 | Sakurai | |
| 5,213,561 A | 5/1993 | Weinstein et al. | |
| 5,246,438 A | 9/1993 | Langberg | |
| 5,248,312 A | 9/1993 | Langberg | |
| 5,275,597 A | 1/1994 | Higgins | |
| 5,277,201 A | 1/1994 | Stern | |
| 5,281,213 A | 1/1994 | Milder | |
| 5,281,217 A | 1/1994 | Edwards | |
| 5,295,955 A | 3/1994 | Rosen | |
| 5,300,099 A | 4/1994 | Rudie | |
| 5,301,687 A | 4/1994 | Wong | |
| 5,314,466 A | 5/1994 | Stern | |
| 5,344,418 A | 9/1994 | Ghaffari | |
| 5,344,435 A | 9/1994 | Turner | |
| 5,348,554 A | 9/1994 | Imran | |
| 5,358,515 A | 10/1994 | Hurter | |
| 5,364,392 A | 11/1994 | Warner | |
| 5,366,490 A | 11/1994 | Edwards | |
| 5,369,251 A | 11/1994 | King | |
| 5,370,678 A | 12/1994 | Edwards | |
| 5,405,346 A | 4/1995 | Grundy | |
| 5,431,649 A | 7/1995 | Mulier | |
| 5,433,740 A | 7/1995 | Yamaguchi | |
| 5,456,684 A | 10/1995 | Schmidt | |
| 5,462,556 A | 10/1995 | Powers | |
| 5,472,423 A | 12/1995 | Gronauer | |
| 5,480,417 A | 1/1996 | Hascoet | |
| 5,489,256 A | 2/1996 | Adair | |
| 5,507,743 A | 4/1996 | Edwards | |
| 5,531,677 A | 7/1996 | Lundquist | |
| 5,540,649 A | 7/1996 | Bonnell | |
| 5,559,295 A | 9/1996 | Sheryll | |
| 5,575,794 A | 11/1996 | Walus | |
| 5,578,029 A | 11/1996 | Trelles | |
| 5,591,227 A | 1/1997 | Dinh | |
| 5,597,146 A | 1/1997 | Putman | |
| 5,599,295 A | 2/1997 | Rosen | |
| 5,599,352 A | 2/1997 | Dinh | |
| 5,603,697 A | 2/1997 | Grundy | |
| 5,620,479 A | 4/1997 | Diederich | |
| 5,643,175 A | 7/1997 | Adair | |
| 5,647,868 A * | 7/1997 | Chinn | A61B 18/02 606/23 |
| 5,647,871 A | 7/1997 | Levine | |
| 5,688,267 A | 11/1997 | Panescu | |
| 5,693,082 A | 12/1997 | Warner | |
| 5,697,949 A | 12/1997 | Giurtino | |
| 5,716,389 A | 2/1998 | Walinsky | |
| 5,737,384 A | 4/1998 | Fenn | |
| 5,741,249 A | 4/1998 | Moss | |
| 5,755,752 A | 5/1998 | Segal | |
| 5,755,754 A | 5/1998 | Rudie | |
| 5,759,200 A | 6/1998 | Azar | |
| 5,776,129 A | 7/1998 | Mersch | |
| 5,776,176 A | 7/1998 | Rudie | |
| 5,782,827 A | 7/1998 | Gough | |
| 5,788,692 A | 8/1998 | Campbell | |
| 5,788,694 A | 8/1998 | Vancaillie | |
| 5,800,494 A | 9/1998 | Campbell | |
| 5,810,803 A | 9/1998 | Moss | |
| 5,810,804 A | 9/1998 | Gough | |
| 5,849,029 A | 12/1998 | Eckhouse | |
| 5,902,251 A | 5/1999 | Vanhooydonk | |
| 5,904,709 A | 5/1999 | Arndt | |
| 5,921,935 A | 7/1999 | Hickey | |
| 5,957,969 A | 9/1999 | Warner | |
| 5,963,082 A | 10/1999 | Dick | |
| 5,995,875 A | 11/1999 | Blewett | |
| 6,002,968 A | 12/1999 | Edwards | |
| 6,012,457 A | 1/2000 | Lesh | |

(56) References Cited

U.S. PATENT DOCUMENTS

| | | |
|---|---|---|
| 6,016,811 A | 1/2000 | Knopp |
| 6,026,331 A | 2/2000 | Feldberg |
| 6,044,846 A | 4/2000 | Edwards |
| 6,056,744 A | 5/2000 | Edwards |
| 6,067,475 A | 5/2000 | Graves |
| 6,073,052 A | 6/2000 | Zelickson |
| 6,083,255 A | 7/2000 | Laufer |
| 6,086,529 A | 7/2000 | Arndt |
| 6,091,995 A | 7/2000 | Ingle et al. |
| 6,097,985 A | 8/2000 | Kasevich |
| 6,102,885 A | 8/2000 | Bass |
| 6,104,959 A | 8/2000 | Spertell |
| 6,106,524 A | 8/2000 | Eggers |
| 6,120,496 A | 9/2000 | Whayne |
| 6,165,163 A | 12/2000 | Chien et al. |
| 6,174,307 B1 | 1/2001 | Daniel et al. |
| 6,181,970 B1 * | 1/2001 | Kasevich .......... A61B 18/18 607/101 |
| 6,182,666 B1 | 2/2001 | Dobak, III |
| 6,188,930 B1 | 2/2001 | Carson |
| 6,190,382 B1 | 2/2001 | Ormsby |
| 6,208,903 B1 | 3/2001 | Richards |
| 6,210,323 B1 | 4/2001 | Gilhuly et al. |
| 6,223,085 B1 | 4/2001 | Dann |
| 6,230,060 B1 | 5/2001 | Mawhinney |
| 6,235,022 B1 | 5/2001 | Hallock |
| 6,241,725 B1 * | 6/2001 | Cosman .......... A61B 18/1477 600/41 |
| 6,245,062 B1 | 6/2001 | Berube |
| 6,246,784 B1 | 6/2001 | Summers |
| 6,246,905 B1 | 6/2001 | Mogul |
| 6,251,128 B1 | 6/2001 | Knopp |
| 6,254,598 B1 | 7/2001 | Edwards |
| 6,273,884 B1 | 8/2001 | Altshuler |
| 6,273,885 B1 | 8/2001 | Koop |
| 6,273,886 B1 | 8/2001 | Edwards |
| 6,277,113 B1 | 8/2001 | Berube |
| 6,287,302 B1 | 9/2001 | Berube |
| 6,306,130 B1 | 10/2001 | Anderson |
| 6,306,132 B1 | 10/2001 | Moorman |
| 6,312,427 B1 | 11/2001 | Berube |
| 6,325,796 B1 | 12/2001 | Berube |
| 6,347,251 B1 * | 2/2002 | Deng .......... A61B 18/1477 606/41 |
| 6,355,033 B1 | 3/2002 | Moorman |
| 6,364,876 B1 | 4/2002 | Erb |
| 6,383,182 B1 | 5/2002 | Berube |
| 6,395,803 B1 | 5/2002 | Angeletakis |
| 6,398,781 B1 | 6/2002 | Goble |
| 6,402,742 B1 | 6/2002 | Blewett |
| 6,427,089 B1 | 7/2002 | Knowlton |
| 6,435,872 B1 | 8/2002 | Nagel |
| 6,461,352 B2 | 10/2002 | Morgan |
| 6,471,696 B1 | 10/2002 | Berube |
| 6,500,174 B1 | 12/2002 | Maguire |
| 6,506,189 B1 | 1/2003 | Rittman |
| 6,514,249 B1 | 2/2003 | Maguire |
| 6,524,308 B1 | 2/2003 | Muller |
| 6,527,768 B2 | 3/2003 | Berube |
| 6,530,922 B2 | 3/2003 | Cosman |
| 6,546,077 B2 | 4/2003 | Chornenky |
| 6,575,969 B1 * | 6/2003 | Rittman, III ....... A61B 18/1482 606/41 |
| 6,577,903 B1 | 6/2003 | Cronin |
| 6,582,426 B2 | 6/2003 | Moorman |
| 6,582,486 B1 | 6/2003 | Delpiano |
| 6,585,733 B2 | 7/2003 | Wellman |
| 6,593,395 B2 | 7/2003 | Angeletakis |
| 6,602,074 B1 | 8/2003 | Suh |
| 6,622,731 B2 | 9/2003 | Daniel |
| 6,635,055 B1 | 10/2003 | Cronin |
| 6,638,277 B2 | 10/2003 | Schaefer et al. |
| 6,652,520 B2 | 11/2003 | Moorman |
| 6,663,625 B1 | 12/2003 | Ormsby |
| 6,666,579 B2 | 12/2003 | Jensen |
| 6,673,068 B1 | 1/2004 | Berube |
| 6,683,625 B2 | 1/2004 | Muthusamy |
| 6,694,163 B1 | 2/2004 | Vining |
| 6,699,240 B2 | 3/2004 | Francischelli |
| 6,702,576 B2 | 3/2004 | Fischer |
| 6,709,271 B2 | 3/2004 | Yin |
| 6,740,107 B2 | 5/2004 | Loeb |
| 6,749,606 B2 | 6/2004 | Keast |
| 6,752,767 B2 | 6/2004 | Turovskiy |
| D493,531 S | 7/2004 | Padain |
| 6,770,070 B1 | 8/2004 | Balbierz |
| 6,780,178 B2 | 8/2004 | Palanker |
| 6,802,840 B2 | 10/2004 | Chin |
| 6,817,976 B2 | 11/2004 | Rovegno |
| 6,817,999 B2 | 11/2004 | Berube |
| 6,823,218 B2 | 11/2004 | Berube |
| 6,837,712 B2 | 1/2005 | Qian |
| 6,847,848 B2 | 1/2005 | Sterzer |
| 6,849,075 B2 | 2/2005 | Bertolero |
| 6,852,091 B2 | 2/2005 | Edwards |
| 6,866,624 B2 | 3/2005 | Chornenky |
| 6,866,663 B2 | 3/2005 | Edwards |
| 6,869,431 B2 | 3/2005 | Maguire et al. |
| 6,878,147 B2 | 4/2005 | Prakash |
| 6,890,968 B2 | 5/2005 | Angeletakis |
| 6,893,436 B2 | 5/2005 | Woodard |
| 6,898,454 B2 | 5/2005 | Atalar |
| D507,649 S | 7/2005 | Padain |
| 6,918,905 B2 | 7/2005 | Neuberger |
| 6,924,325 B2 | 8/2005 | Qian |
| 6,957,108 B2 | 10/2005 | Turner |
| 6,962,586 B2 | 11/2005 | Berube |
| 6,972,016 B2 | 12/2005 | Hill |
| 6,976,986 B2 | 12/2005 | Berube |
| 6,994,546 B2 | 2/2006 | Fischer |
| 7,022,105 B1 | 4/2006 | Edwards |
| 7,033,352 B1 | 4/2006 | Gauthier |
| 7,097,641 B1 | 8/2006 | Arless |
| 7,101,369 B2 | 9/2006 | Van der Welde |
| 7,115,126 B2 | 10/2006 | Berube |
| 7,128,739 B2 | 10/2006 | Prakash |
| 7,142,633 B2 | 11/2006 | Eberhard |
| 7,147,632 B2 | 12/2006 | Prakash |
| 7,153,298 B1 | 12/2006 | Cohen |
| 7,156,842 B2 | 1/2007 | Sartor |
| 7,160,289 B2 | 1/2007 | Cohen |
| 7,160,292 B2 | 1/2007 | Moorman |
| 7,182,762 B2 | 2/2007 | Bortkiewicz |
| 7,184,824 B2 | 2/2007 | Hashimshony |
| 7,197,363 B2 | 3/2007 | Prakash |
| 7,233,820 B2 | 6/2007 | Gilboa |
| 7,244,254 B2 | 7/2007 | Brace |
| 7,263,997 B2 | 9/2007 | Madsen et al. |
| 7,266,407 B2 | 9/2007 | Li et al. |
| 7,282,049 B2 | 10/2007 | Orszulak |
| 7,311,703 B2 | 12/2007 | Turovskiy |
| 7,318,824 B2 | 1/2008 | Prakash |
| 7,324,104 B1 | 1/2008 | Bitter |
| 7,331,960 B2 | 2/2008 | Schaer |
| 7,381,208 B2 | 6/2008 | Van der Walt |
| 7,400,929 B2 | 7/2008 | Zelickson et al. |
| 7,402,140 B2 | 7/2008 | Spero |
| 7,410,484 B2 | 8/2008 | Littrup |
| 7,467,015 B2 | 12/2008 | Van der Weide |
| 7,473,219 B1 | 1/2009 | Glenn |
| 7,527,623 B2 | 5/2009 | Prakash |
| 7,594,313 B2 | 9/2009 | Prakash |
| 7,601,149 B2 | 10/2009 | DiCarlo |
| 7,625,369 B2 | 12/2009 | Abboud |
| 7,722,620 B2 | 5/2010 | Truckai |
| 7,731,677 B2 | 6/2010 | Sakurai |
| 7,815,637 B2 | 10/2010 | Ormsby |
| 7,826,904 B2 | 11/2010 | Appling |
| 7,862,559 B2 | 1/2011 | Prakash |
| 7,875,024 B2 | 1/2011 | Turovskiy |
| 8,035,570 B2 | 10/2011 | Prakash |
| 8,059,059 B2 | 11/2011 | Bonn |
| 8,093,500 B2 | 1/2012 | Deborski |
| 8,109,895 B2 | 2/2012 | Williams et al. |

(56) References Cited

U.S. PATENT DOCUMENTS

| | | |
|---|---|---|
| 8,147,511 B2 | 4/2012 | Perry |
| 8,152,799 B2 | 4/2012 | Ormsby |
| 8,155,418 B2 | 4/2012 | Delso |
| 8,235,981 B2 | 8/2012 | Prakash |
| 8,357,148 B2 | 1/2013 | Boulais et al. |
| 8,403,924 B2 | 3/2013 | Behnke |
| 8,430,871 B2 | 4/2013 | Brannan |
| 8,454,589 B2 | 6/2013 | Deno |
| 8,515,554 B2 | 8/2013 | Carr |
| 8,523,854 B2 | 9/2013 | Willyard |
| 8,540,710 B2 | 9/2013 | Johnson |
| 8,574,227 B2 | 11/2013 | Hancock |
| 8,643,561 B2 | 2/2014 | Prakash |
| 8,653,828 B2 | 2/2014 | Hancock |
| 8,655,454 B2 | 2/2014 | Prakash |
| 8,672,932 B2 | 3/2014 | van der Weide |
| 8,747,398 B2 | 6/2014 | Behnke |
| 8,764,744 B2 | 7/2014 | Brannan |
| 8,932,281 B2 | 1/2015 | Brannan |
| 8,934,989 B2 | 1/2015 | Ormsby |
| 8,945,111 B2 | 2/2015 | Brannan et al. |
| 8,968,290 B2 | 3/2015 | Brannan |
| 9,008,793 B1 | 4/2015 | Cosman |
| 9,011,421 B2 | 4/2015 | Brannan |
| 9,017,319 B2 | 4/2015 | Brannan |
| 9,041,616 B2 | 5/2015 | Prakash |
| 9,072,532 B2 | 7/2015 | van der Weide |
| 9,113,926 B2 | 8/2015 | Brannan |
| 9,119,649 B2 | 9/2015 | van der Weide |
| 9,119,650 B2 | 9/2015 | Brannan |
| 9,161,811 B2 | 10/2015 | Cronin |
| 9,173,706 B2 | 11/2015 | Rossetto |
| 9,192,436 B2 | 11/2015 | Willyard |
| 9,192,438 B2 | 11/2015 | Thiel |
| 9,198,725 B2 | 12/2015 | Willyard |
| 9,220,441 B2 | 12/2015 | Yoo |
| 2001/0020166 A1 | 9/2001 | Daly et al. |
| 2001/0039416 A1 | 11/2001 | Moorman et al. |
| 2001/0049524 A1 | 12/2001 | Morgan |
| 2002/0022836 A1 | 2/2002 | Goble |
| 2002/0026187 A1 | 2/2002 | Swanson |
| 2002/0026188 A1 | 2/2002 | Balbierz et al. |
| 2002/0040185 A1 | 4/2002 | Atalar et al. |
| 2002/0072742 A1 | 6/2002 | Schaefer |
| 2002/0087151 A1 | 7/2002 | Mody |
| 2002/0087157 A1 | 7/2002 | Sliwa et al. |
| 2002/0173780 A1 | 11/2002 | Altshuler |
| 2002/0183740 A1 | 12/2002 | Edwards |
| 2003/0032951 A1 | 2/2003 | Rittman et al. |
| 2003/0060813 A1 | 3/2003 | Loeb |
| 2003/0065317 A1 | 4/2003 | Rudie |
| 2003/0088242 A1 | 5/2003 | Prakash |
| 2003/0120268 A1 | 6/2003 | Bertolero |
| 2003/0130711 A1 | 7/2003 | Pearson et al. |
| 2004/0030367 A1 | 2/2004 | Yamaki et al. |
| 2004/0068208 A1 | 4/2004 | Cimino et al. |
| 2004/0082859 A1 | 4/2004 | Schaer |
| 2004/0116921 A1 | 6/2004 | Sherman |
| 2004/0133254 A1 | 7/2004 | Sterzer |
| 2004/0158237 A1 | 8/2004 | Abboud |
| 2004/0186517 A1 | 9/2004 | Hill et al. |
| 2004/0199154 A1 | 10/2004 | Nahon |
| 2004/0215131 A1 | 10/2004 | Sakurai et al. |
| 2004/0215294 A1 | 10/2004 | Littrup et al. |
| 2004/0243004 A1 | 12/2004 | Carr |
| 2004/0243200 A1 | 12/2004 | Turner |
| 2004/0267248 A1 | 12/2004 | Duong |
| 2005/0011885 A1 | 1/2005 | Seghatol |
| 2005/0015081 A1 | 1/2005 | Turovskiy |
| 2005/0075629 A1 | 4/2005 | Chapelon |
| 2005/0107870 A1 | 5/2005 | Wang |
| 2005/0109900 A1 | 5/2005 | Schilt et al. |
| 2005/0113824 A1 | 5/2005 | Sartor |
| 2005/0143726 A1 | 6/2005 | Bortkiewicz |
| 2005/0149010 A1 | 7/2005 | Turovskiy |
| 2005/0165389 A1 | 7/2005 | Swain |
| 2005/0177209 A1 | 8/2005 | Leung et al. |
| 2005/0245919 A1 | 11/2005 | van der Welde |
| 2005/0245920 A1 | 11/2005 | Vitullo et al. |
| 2006/0064083 A1 | 3/2006 | Khalaj et al. |
| 2006/0079886 A1 | 4/2006 | Orszulak et al. |
| 2006/0094956 A1 | 5/2006 | Vismanathan |
| 2006/0106281 A1 | 5/2006 | Boulais |
| 2006/0122625 A1 | 6/2006 | Truckai |
| 2006/0129140 A1 | 6/2006 | Todd et al. |
| 2006/0155270 A1 | 7/2006 | Hancock |
| 2006/0171506 A1 | 8/2006 | Lovoi et al. |
| 2006/0189973 A1 | 8/2006 | van der Weide |
| 2006/0200026 A1 | 9/2006 | Wallace et al. |
| 2006/0200120 A1 | 9/2006 | DiCarlo |
| 2006/0224220 A1 | 10/2006 | Zelickson |
| 2006/0264921 A1 | 11/2006 | Deutsch |
| 2006/0276780 A1 | 12/2006 | Brace |
| 2006/0289528 A1 | 12/2006 | Chiu |
| 2007/0016180 A1 | 1/2007 | Lee, Jr. et al. |
| 2007/0021741 A1 | 1/2007 | Marwan et al. |
| 2007/0066972 A1 | 3/2007 | Ormsby |
| 2007/0185554 A1 | 8/2007 | Appling |
| 2007/0203551 A1 | 8/2007 | Cronin |
| 2007/0208389 A1 | 9/2007 | Amundson et al. |
| 2007/0230757 A1 | 10/2007 | Trachtenberg et al. |
| 2007/0270924 A1 | 11/2007 | McCann et al. |
| 2007/0276362 A1 | 11/2007 | Rioux |
| 2007/0282319 A1 | 12/2007 | van der Weide |
| 2007/0288079 A1 | 12/2007 | van der Weide |
| 2008/0033424 A1 | 2/2008 | Van Der Weide |
| 2008/0045938 A1 | 2/2008 | Weide et al. |
| 2008/0114345 A1 | 5/2008 | Arless et al. |
| 2008/0147056 A1 | 6/2008 | Van der Weide |
| 2008/0161890 A1 | 7/2008 | Lafontaine |
| 2008/0188868 A1 | 8/2008 | Weitzner et al. |
| 2008/0188869 A1 | 8/2008 | Weitzner et al. |
| 2008/0188871 A1 | 8/2008 | Smith et al. |
| 2008/0188890 A1 | 8/2008 | Weitzner et al. |
| 2008/0195226 A1 | 8/2008 | Williams et al. |
| 2008/0221391 A1 | 9/2008 | Weitzner et al. |
| 2008/0243176 A1 | 10/2008 | Weitzner et al. |
| 2009/0005766 A1 | 1/2009 | Brannan |
| 2009/0054962 A1 | 2/2009 | Lefler |
| 2009/0076492 A1 | 3/2009 | Behnke |
| 2009/0105579 A1* | 4/2009 | Garibaldi ............... A61B 8/483 382/128 |
| 2009/0118725 A1 | 5/2009 | Auth et al. |
| 2009/0171203 A1* | 7/2009 | Avital .................... A61B 18/02 606/130 |
| 2009/0187180 A1 | 7/2009 | Brannan |
| 2009/0187186 A1 | 7/2009 | Jakus |
| 2009/0196480 A1 | 8/2009 | Nields et al. |
| 2009/0222002 A1 | 9/2009 | Bonn |
| 2009/0281536 A1 | 11/2009 | Beckman et al. |
| 2009/0306644 A1 | 12/2009 | Mayse et al. |
| 2010/0023866 A1 | 1/2010 | Peck |
| 2010/0045558 A1 | 2/2010 | Rossetto |
| 2010/0045559 A1 | 2/2010 | Rossetto |
| 2010/0076424 A1 | 3/2010 | Carr |
| 2010/0081928 A1 | 4/2010 | Hyde |
| 2010/0137796 A1 | 6/2010 | Perry et al. |
| 2010/0228244 A1 | 9/2010 | Hancock |
| 2010/0268223 A1 | 10/2010 | Coe |
| 2010/0286791 A1 | 11/2010 | Goldsmith |
| 2010/0292766 A1 | 11/2010 | Duong |
| 2010/0305561 A1 | 12/2010 | Prakash et al. |
| 2010/0312095 A1 | 12/2010 | Jenkins |
| 2010/0312096 A1 | 12/2010 | Guttman |
| 2010/0317962 A1 | 12/2010 | Jenkins |
| 2011/0077635 A1 | 3/2011 | Bonn et al. |
| 2011/0098696 A1 | 4/2011 | Brannan |
| 2011/0118723 A1 | 5/2011 | Turner et al. |
| 2011/0118725 A1 | 5/2011 | Mayse |
| 2011/0213352 A1 | 9/2011 | Lee et al. |
| 2011/0238060 A1 | 9/2011 | Lee, Jr. |
| 2011/0238061 A1 | 9/2011 | van der Weide |
| 2011/0257647 A1 | 10/2011 | Mayse |
| 2011/0301587 A1 | 12/2011 | Deem |

(56) References Cited

U.S. PATENT DOCUMENTS

| | | |
|---|---|---|
| 2012/0016358 A1 | 1/2012 | Mayse |
| 2012/0053577 A1 | 3/2012 | Lee et al. |
| 2012/0116286 A1 | 5/2012 | Williams et al. |
| 2012/0182134 A1 | 7/2012 | Doyle |
| 2012/0194409 A1 | 8/2012 | Brannan |
| 2012/0203216 A1 | 8/2012 | Mayse |
| 2012/0203222 A1 | 8/2012 | Mayse |
| 2012/0209257 A1 | 8/2012 | Weide et al. |
| 2012/0209261 A1 | 8/2012 | Mayse |
| 2012/0209296 A1 | 8/2012 | Mayse |
| 2012/0232544 A1 | 9/2012 | Willyard |
| 2012/0232549 A1 | 9/2012 | Willyard |
| 2012/0277763 A1* | 11/2012 | Greenblatt ............ A61B 18/12 607/101 |
| 2012/0310228 A1 | 12/2012 | Bonn et al. |
| 2012/0316551 A1 | 12/2012 | van der Weide |
| 2012/0316552 A1 | 12/2012 | Mayse |
| 2012/0316559 A1 | 12/2012 | Mayse |
| 2013/0004037 A1 | 1/2013 | Scheuering |
| 2013/0023866 A1 | 1/2013 | Stringham et al. |
| 2013/0072924 A1 | 3/2013 | Burgener |
| 2013/0116679 A1 | 5/2013 | van der Weide et al. |
| 2013/0123598 A1 | 5/2013 | Jenkins |
| 2013/0131496 A1 | 5/2013 | Jenkins |
| 2013/0165915 A1 | 6/2013 | Thiel |
| 2013/0259335 A1 | 10/2013 | Mallya et al. |
| 2013/0306543 A1 | 11/2013 | Beisser |
| 2013/0338530 A1 | 12/2013 | Kassab |
| 2014/0005706 A1 | 1/2014 | Gelfand et al. |
| 2014/0046176 A1 | 2/2014 | Ladtkow |
| 2014/0152656 A1 | 6/2014 | Yoo |
| 2014/0163664 A1 | 6/2014 | Goldsmith et al. |
| 2014/0276033 A1 | 9/2014 | Brannan |
| 2014/0276200 A1 | 9/2014 | Brannan |
| 2014/0046174 A1 | 12/2014 | Ladtkow et al. |
| 2015/0148792 A1 | 5/2015 | Kim |
| 2015/0150628 A1 | 6/2015 | Buysse |
| 2015/0164587 A1 | 6/2015 | Bonn et al. |
| 2015/0190193 A1 | 7/2015 | Mayse |
| 2015/0250540 A1 | 9/2015 | Behdad et al. |
| 2015/0351839 A1 | 12/2015 | Brannan |
| 2015/0374438 A1 | 12/2015 | van der Weide |

FOREIGN PATENT DOCUMENTS

| | | |
|---|---|---|
| CN | 1593353 | 3/2005 |
| CN | 1703168 | 11/2005 |
| CN | 2753408 | 1/2006 |
| CN | 201267529 | 7/2009 |
| CN | 101511295 | 8/2009 |
| CN | 101563042 | 10/2009 |
| EP | 1186274 | 3/2002 |
| EP | 1265532 | 12/2002 |
| EP | 1395190 | 3/2004 |
| EP | 1450710 | 9/2004 |
| EP | 1499251 | 1/2005 |
| EP | 1542607 | 6/2005 |
| EP | 1723922 A | 11/2006 |
| EP | 2098184 | 9/2009 |
| EP | 2295000 | 3/2011 |
| EP | 2316370 | 5/2011 |
| EP | 1659969 | 10/2012 |
| GB | 2388039 | 11/2003 |
| GB | 2406521 | 4/2005 |
| JP | 10-192286 | 7/1998 |
| JP | 2002-541884 | 12/2002 |
| JP | 2003-530139 | 10/2003 |
| JP | 2003-534037 | 11/2003 |
| JP | 2004-188179 | 7/2004 |
| JP | 2005-522274 | 7/2005 |
| JP | 2007-029457 | 2/2007 |
| JP | 2007-532024 | 11/2007 |
| JP | 2008-142467 | 6/2008 |
| JP | 2009-006150 | 1/2009 |
| JP | 2009-521264 | 6/2009 |
| JP | 2009-521967 | 6/2009 |
| JP | 2009-207898 | 9/2009 |
| JP | 2009-285463 | 12/2009 |
| JP | 2010-505573 | 2/2010 |
| JP | 2009-521967 | 3/2010 |
| JP | 2010-050975 | 3/2010 |
| JP | 2011-511538 | 4/2011 |
| JP | 2011-092720 | 5/2011 |
| JP | 2011-152414 | 8/2011 |
| WO | WO 92/04934 | 4/1992 |
| WO | WO 93/09845 | 5/1993 |
| WO | WO 95/004385 | 9/1995 |
| WO | WO 97/48449 | 12/1997 |
| WO | WO 99/56643 | 11/1999 |
| WO | WO 00/57811 | 10/2000 |
| WO | WO 01/70114 | 9/2001 |
| WO | WO 03/039385 | 5/2003 |
| WO | 2003/086190 | 10/2003 |
| WO | WO 03/086498 | 10/2003 |
| WO | WO 03/088806 | 10/2003 |
| WO | WO 03/088858 | 10/2003 |
| WO | WO 2004/004586 | 1/2004 |
| WO | WO 04026122 | 1/2004 |
| WO | WO 04/033039 | 4/2004 |
| WO | WO 2004/084748 | 10/2004 |
| WO | WO 04/112628 | 12/2004 |
| WO | WO 2005/011049 | 2/2005 |
| WO | WO 05/034783 | 4/2005 |
| WO | WO 05/110265 | 11/2005 |
| WO | 2006/002843 | 1/2006 |
| WO | WO 06/002943 | 1/2006 |
| WO | WO 06/005579 | 1/2006 |
| WO | WO 06/008481 | 1/2006 |
| WO | WO 2006/002843 | 1/2006 |
| WO | WO 2006/084676 | 8/2006 |
| WO | 2006/127847 | 11/2006 |
| WO | WO 2006/12149 | 11/2006 |
| WO | WO 2006/127847 | 11/2006 |
| WO | 2007/076924 | 7/2007 |
| WO | WO 2007/076924 | 7/2007 |
| WO | WO 2007/112103 | 10/2007 |
| WO | WO 2008/008545 | 1/2008 |
| WO | WO 2008/044013 | 4/2008 |
| WO | WO 08/142686 | 11/2008 |
| WO | 2010/067360 | 6/2010 |
| WO | WO 2010/067360 | 6/2010 |
| WO | WO 11/008903 | 1/2011 |
| WO | 2011/017168 | 2/2011 |
| WO | WO 2011/017168 | 2/2011 |
| WO | WO 2011/140087 | 11/2011 |
| WO | 2013/173481 | 11/2013 |
| WO | WO 2013/173481 | 11/2013 |

OTHER PUBLICATIONS

European Search Report, EP Patent Application No. 17168163.8, dated Sep. 13, 2017.

Guy, AW (1971) IEEE Trans. Microwave Theory Tech. 19 pp. 205-214.

European Search Report dated Mar. 9, 2015, EP Patent Application No. 14189493.1.

Extended European Search Report, EP Patent Application No. 11778168 dated Sep. 24, 2013.

Notice Regarding Extended European Search Report, EP Patent Application No. 11778168 dated Oct. 2, 2013.

International Preliminary Report on Patentability re: PCT/US2007/007408 dated Sep. 30, 2008.

International Preliminary Report on Patentability re: PCT/US2016/058888 dated Dec. 11, 2017.

International Preliminary Report on Patentability re: PCT/US2016/058890 dated May 11, 2018.

International Search Report re: PCT/US2007/007408 dated Aug. 31, 2007.

Guy, AW (1971) IEEE Trans. Microwave Theory Tech. 19 pp. 189-217.

(56) References Cited

OTHER PUBLICATIONS

"Carbon dioxide." Carbon dioxide—New World Encyclopedia. Web. <http://www.newworldencyclopedia.org/entry/Carbon_dioxide>.
International Patent Application No. PCT/US05/14534 dated Nov. 29, 2005.
International Preliminary Report on Patentability re: PCT/US2007/007464 dated Sep. 30, 2008.
International Search Report PCT/US2006/028821 dated Mar. 21, 2007.
International Search Report on Patentability re: PCT/US2007/016082 dated Jul. 21, 2008.
International Search Report PCT/US2011/035000 dated Jan. 6, 2012.
International Search Report re: PCT/US2012/071310 dated Feb. 25, 2013.
International Search Report re: PCT/US16/58888 dated Feb. 15, 2017.
International Search Report re: PCT/US2016/058890 dated Jan. 19, 2017.
International Preliminary Report on Patentability re: PCT/US2007/016082 dated Jan. 14, 2009.
International Preliminary Report on Patentability re: PCT/US2010/043558 dated Jan. 31, 2012.
International Preliminary Report on Patentability re: PCT/US2011/035000 dated Nov. 6, 2012.
International Preliminary Report on Patentability re: PCT/US2012/071310 dated Aug. 19, 2014.
Supplementary European Search Report re: EP07810483 dated Mar. 22, 2013.
Supplementary European Search Report re: EP10806929 dated Feb. 21, 2013.
Supplementary European Search Report re: EP11778168 dated Sep. 24, 2013.
Supplementary European Search Report re: EP12860249 dated Sep. 15, 2015.
U.S. Appl. No. 09/847,181, filed May 1, 2001.
U.S. Appl. No. 10/370,179, filed Feb. 19, 2003.
U.S. Appl. No. 10/834,802, filed Apr. 29, 2004.
U.S. Appl. No. 10/961,761, filed Oct. 7, 2004.
U.S. Appl. No. 10/961,994, filed Oct. 7, 2004.
U.S. Appl. No. 10/980,699, filed Nov. 3, 2004.
U.S. Appl. No. 11/053,987, filed Feb. 8, 2005.
U.S. Appl. No. 11/236,985, filed Sep. 28, 2005.
U.S. Appl. No. 11/237,136, filed Sep. 28, 2005.
U.S. Appl. No. 11/237,430, filed Sep. 28, 2005.
U.S. Appl. No. 11/440,331, filed May 24, 2006.
U.S. Appl. No. 11/452,637, filed Jun. 14, 2006.
U.S. Appl. No. 11/502,783, filed Aug. 11, 2006.
U.S. Appl. No. 11/514,628, filed Sep. 1, 2006.
U.S. Appl. No. 11/728,428, filed Mar. 26, 2007.
U.S. Appl. No. 11/728,457, filed Mar. 26, 2007.
U.S. Appl. No. 11/728,460, filed Mar. 26, 2007.
U.S. Appl. No. 60/679,722, filed May 10, 2005.
U.S. Appl. No. 60/785,466, filed Mar. 24, 2006.
U.S. Appl. No. 60/785,467, filed Mar. 24, 2006.
U.S. Appl. No. 60/785,690, filed Mar. 24, 2006.
U.S. Appl. No. 60/831,055, filed Jul. 14, 2006.
Brace Christopher et al. "Analysis and experimental validation of a triaxial antenna for microwave tumor ablation" IEEE MTTS Int Microw Symp. Jun. 3, 2004(6-11) 1437-1440.
Brace Christopher et al. "Microwave Ablation with a Triaxial Antenna: Results in ex vivo Bovine Liver" IEEE Transations on Microwave Theory and Techniques vol. 53 No. Jan. 1, 2005.
English translation of a Decision of Refusal from related Japanese Patent Application No. 2013-509179 dated Jun. 30, 2015.
European Search Report dated Mar. 3, 2009 EP Patent Application No. 06 802 385.2.
Golio "The RF and microwave handbook" Edition: 2. Published by CRC Press 2001 ISBN 0849338592X 97808493859626.
Head Hayden W. et al. "Thermal Ablation for Hepatocellular Carcinoma" Gastroenterology 2004:127:S167-S178.
International Search Report PCT/US06/031644 dated Aug. 17, 2007.
International Search Report PCT/US06/032811 dated Jan. 25, 2007.
International Search Report PCT/US2005/014534 dated Nov. 29, 2005.
International Search Report PCT/US2006/017981 dated Sep. 7, 2006.
International Search Report PCT/US2006/033341 dated Aug. 17, 2007.
Seki Toshihito et al. "Ultrasonically Guided Percutaneous Microwave Coagulation Therapy for Small Hepatocellular Carcinoma" Cancer Aug. 1, 1994 vol. 74 No. 3 pp. 817-825.
European Search Report, EP Patent Application No. 06802385.2, dated Mar. 3, 2009.
European Search Report, EP Patent Application No. 11778168, dated Oct. 2, 2013.
International Preliminary Report on Patentability, PCT/US2007/007464, dated Sep. 30, 2008.
International Search Report, PCT/US2007/016082, dated Jul. 21, 2008.
International Search Report, PCT/US2012/071310, dated Feb. 25, 2013.
International Preliminary Report on Patentability, PCT/US2007/016082, dated Jan. 14, 2009.
International Preliminary Report on Patentability, PCT/US2010/043558, dated Jan. 31, 2012.
International Preliminary Report on Patentability, PCT/US2011/035000, dated Nov. 6, 2012.
International Preliminary Report on Patentability, PCT/US2012/071310, dated Aug. 19, 2014.
European Search Report, EP Patent Application No. 07810483, dated Mar. 22, 2013.
European Search Report, EP Patent Application No. 10806929.5, dated Feb. 21, 2013.
European Search Report, EP Patent Application No. 12860249.7, dated Sep. 15, 2015.

* cited by examiner

ENERGY DELIVERY SYSTEMS AND USES THEREOF

The present application is a continuation of pending U.S. patent application Ser. No. 11/879,070, filed Jul. 16, 2007, which claims priority to U.S. Provisional Application Ser. Nos. 60/831,056, filed Jul. 14, 2006, and 60/853,911, filed Oct. 24, 2006, each herein incorporated by reference in their entireties.

FIELD OF THE INVENTION

The present invention relates to comprehensive systems, devices and methods for delivering energy to tissue for a wide variety of applications, including medical procedures (e.g., tissue ablation, resection, cautery, vascular thrombosis, treatment of cardiac arrhythmias and dysrhythmias, electrosurgery, tissue harvest, etc.). In certain embodiments, systems, devices, and methods are provided for treating a tissue region (e.g., a tumor) through application of energy.

BACKGROUND

Ablation is an important therapeutic strategy for treating certain tissues such as benign and malignant tumors, cardiac arrhythmias, cardiac dysrhythmias and tachycardia. Most approved ablation systems utilize radio frequency (RF) energy as the ablating energy source. Accordingly, a variety of RF based catheters and power supplies are currently available to physicians. However, RF energy has several limitations, including the rapid dissipation of energy in surface tissues resulting in shallow "burns" and failure to access deeper tumor or arrhythmic tissues. Another limitation of RF ablation systems is the tendency of eschar and clot formation to form on the energy emitting electrodes which limits the further deposition of electrical energy.

Microwave energy is an effective energy source for heating biological tissues and is used in such applications as, for example, cancer treatment and preheating of blood prior to infusions. Accordingly, in view of the drawbacks of the traditional ablation techniques, there has recently been a great deal of interest in using microwave energy as an ablation energy source. The advantage of microwave energy over RF is the deeper penetration into tissue, insensitivity to charring, lack of necessity for grounding, more reliable energy deposition, faster tissue heating, and the capability to produce much larger thermal lesions than RF, which greatly simplifies the actual ablation procedures. Accordingly, there are a number of devices under development that utilize electromagnetic energy in the microwave frequency range as the ablation energy source (see, e.g., U.S. Pat. Nos. 4,641,649, 5,246,438, 5,405,346, 5,314,466, 5,800,494, 5,957,969, 6,471,696, 6,878,147, and 6,962,586; each of which is herein incorporated by reference in their entireties).

Unfortunately, current devices configured to deliver microwave energy have drawbacks. For example, current devices produce relatively small lesions because of practical limits in power and treatment time. Current devices have power limitations in that the power carrying capacity of the feedlines are small. Larger diameter feedlines are undesirable, however, because they are less easily inserted percutaneously and may increase procedural complication rates. Microwave devices are also limited to single antennas for most purposes thus limiting the ability to simultaneously treat multiple areas or to place several antennas in close proximity to create large zones of tissue heating. In addition, heating of the feedline at high powers can lead to burns around the area of insertion for the device.

Improved systems and devices for delivering energy to a tissue region are needed. In addition, improved systems and devices capable of delivering microwave energy without corresponding microwave energy loss are needed. In addition, systems and devices capable of percutaneous delivery of microwave energy to a subject's tissue without undesired tissue burning are needed. Furthermore, systems for delivery of desired amounts of microwave energy without requiring physically large invasive components are needed.

SUMMARY OF THE INVENTION

The present invention relates to comprehensive single and multiple antenna systems, devices and methods for delivering energy to tissue for a wide variety of applications, including medical procedures (e.g., tissue ablation, resection, cautery, vascular thrombosis, treatment of cardiac arrhythmias and dysrhythmias, electrosurgery, tissue harvest, etc.). In certain embodiments, systems, devices, and methods are provided for treating a tissue region (e.g., a tumor) through application of energy.

The present invention provides systems, devices, and methods that employ components for the delivery of energy to a tissue region (e.g., tumor, lumen, organ, etc.). In some embodiments, the system comprises an energy delivery device and one or more of: a processor, a power supply, a power splitter, an imaging system, a tuning system, and a temperature adjustment system.

The present invention is not limited to a particular type of energy delivery device. The present invention contemplates the use of any known or future developed energy delivery device in the systems of the present invention. In some embodiments, existing commercial energy delivery devices are utilized. In other embodiments, improved energy delivery devices having an optimized characteristic (e.g., small size, optimized energy delivery, optimized impedance, optimized heat dissipation, etc.) are used. In some such embodiments, the energy delivery device is configured to deliver energy (e.g., microwave energy) to a tissue region. In some embodiments, the energy delivery devices are configured to deliver microwave energy at an optimized characteristic impedance (e.g., configured to operate with a characteristic impedance higher than 50Ω) (e.g., between 50 and 90Ω; e.g., higher than 50, . . . , 55, 56, 57, 58, 59, 60, 61, 62, . . . 90Ω, preferably at 77Ω) (see, e.g., U.S. patent application Ser. No. 11/728,428; herein incorporated by reference in its entirety).

A significant source of undesired overheating of the device is the dielectric heating of the insulator, potentially resulting in tissue damage. The energy delivery devices of the present invention are designed to prevent undesired device overheating. The energy delivery devices are not limited to a particular manner of preventing undesired device heating. In some embodiments, the devices employ circulation of coolant. In some embodiments, the devices are configured to detect an undesired rise in temperature within the device (e.g., along the outer conductor) and automatically or manually reduce such an undesired temperature rise through flowing of coolant through the coolant passage channels.

In some embodiments, the energy delivery devices have improved cooling characteristics. For example, in some embodiments, the devices permit the use of coolant without increasing the diameter of the device. This is in contrast to existing devices that flow coolant through an external sleeve or otherwise increase the diameter of the device to accommodate the flow of a coolant. In some embodiments, the energy delivery devices have therein one or more coolant passage channels for purposes of reducing unwanted heat dissipation (see, e.g., U.S. patent application Ser. No. 11/728,460; herein incorporated by reference in its entirety). In some embodiments, the energy delivery devices have therein a tube (e.g., needle, plastic tube, etc.) that runs the length of or partially runs the length of the device, designed to prevent device overheating through circulation of coolant material. In some embodiments, channels or tubes displace material from a dielectric component located between the inner and outer conductors of a coaxial cable. In some embodiments, channels or tubes replace the dielectric material or substantially replace the dielectric material. In some embodiments, channel or tubes displace a portion of the outer conductor. For example, in some embodiments, a portion of the outer conductor is removed or shaved off to generate a passageway for the flow of coolant. One such embodiments is shown in FIG. 12. In this embodiments, a coaxial cable 900 has an outer conductor 910, an inner conductor 920, and a dielectric material 930. In this embodiments, a region 940 of the dielectric material is removed, creating space for coolant flow. The only remaining outer conductor material the circumscribes or substantially circumscribes the coaxial cable is at distal 950 and proximal 960 end regions. A thin strip of conductive material 970 connects the distal 950 and proximal 960 end regions. In this embodiments, a thin channel 980 is cut from the conductive material at the proximal end region 960 to permit coolant flow into the region where the outer conductive material was removed (or was manufacture to be absent) 940. The present invention is not limited by the size or shape of the passageway, so long as coolant can be delivered. For example, in some embodiments, the passageway is a linear path that runs the length of the coaxial cable. In some embodiments, spiral channels are employed. In some embodiments, the tube or channel displaces or replaces at least a portion of the inner conductor. For example, large portions of the inner conductor may be replaced with a coolant channel, leaving only small portions of metal near the proximal and distal ends of the device to permit tuning, wherein the portions are connected by a thin strip of conducting material. In some embodiments, a region of interior space is created within the inner or outer conductor to create one or more channels for coolant. For example, the inner conductor may be provided as a hollow tube of conductive material, with a coolant channel provided in the center. In such embodiments, the inner conductor can be used either for inflow or outflow (or both) of coolant.

In some embodiments, where a coolant tube is placed within the device, the tube has multiple channels for intake and outtake of coolant through the device. The device is not limited to a particular positioning of the tube (e.g., coolant needle) within the dielectric material. In some embodiments, the tube is positioned along the outside edge of the dielectric material, the middle of the dielectric material, or at any location within the dielectric material. In some embodiments, the dielectric material is pre-formed with a channel designed to receive and secure the tube. In some embodiments, a handle is attached with the device, wherein the handle is configured to, for example, control the passing of coolant into and out of the tube. In some embodiments, the tube is flexible. In some embodiments, the tube is inflexible. In some embodiments, the portions of the tube are flexible, while other portions are inflexible. In some embodiments, the tube is compressible. In some embodiments, the tube is incompressible. In some embodiments, portions of the tube are compressible, while other portions are incompressible. The tube is not limited to a particular shape or size. In some embodiments, wherein the tube is a coolant needle (e.g., a 29 gauge needle or equivalent size) that fits within a coaxial cable having a diameter equal or less than a 12 gauge needle. In some embodiments, the exterior of the tube has a coating of adhesive and/or grease so as to secure the tube or permit sliding movement within the device. In some embodiments, the tube has one or more holes along its length that permit release of coolant into desired regions of the device. In some embodiments, the holes are initially blocked with a meltable material, such that a particular threshold of heat is required to melt the material and release coolant through the particular hole or holes affected. As such, coolant is only released in areas that have reached the threshold head level.

In some embodiments, coolant is preloaded into the antenna, handle or other component of the devices of the present invention. In other embodiments, the coolant is added during use. In some pre-loaded embodiments, a liquid coolant is preloaded into, for example, the distal end of the antenna under conditions that create a self-perpetuating vacuum. In some such embodiments, as the liquid coolant vaporizes, more fluid is drawn in by the vacuum.

The present invention is not limited by the nature of the coolant material employed. Coolants included, but are not limited to, liquids and gasses. Exemplary coolant fluids include, but are not limited to, one or more of or combinations of, water, glycol, air, inert gasses, carbon dioxide, nitrogen, helium, sulfur hexafluoride, ionic solutions (e.g., sodium chloride with or without potassium and other ions), dextrose in water, Ringer's lactate, organic chemical solutions (e.g., ethylene glycol, diethylene glycol, or propylene glycol), oils (e.g., mineral oils, silicone oils, fluorocarbon oils), liquid metals, freons, halomethanes, liquified propane, other haloalkanes, anhydrous ammonia, sulfur dioxide. In some embodiments, cooling occurs, at least in part, by changing concentrations of coolant, pressure, or volume. For example, cooling can be achieved via gas coolants using the Joule-Thompson effect. In some embodiments, the cooling is provided by a chemical reaction. The devices are not limited to a particular type of temperature reducing chemical reaction. In some embodiments, the temperature reducing chemical reaction is an endothermic reaction. The devices are not limited to a particular manner of applying endothermic reactions for purposes of preventing undesired heating. In some embodiments, first and second chemicals are flowed into the device such that they react to reduce the temperature of the device. In some embodiments, the device is prepared with the first and second chemicals preloaded in the device. In some embodiments, the chemicals are separated by a barrier that is removed when desired. In some embodiments, the barrier is configured to melt upon exposure to a predetermined temperature or temperature range. In such embodiments, the device initiates the endothermical reaction only upon reaching a heat level that merits cooling. In some embodiments, multiple different barriers are located throughout the device such that local cooling occurs only at those portions of the device where undesired heating is occurring. In some embodiment, the barriers used are beads that encompass one of the two chemicals. In some embodiments, the barriers are walls (e.g., discs in the shape of washers) that melt to combine the two chemicals. In some embodiments, the barriers are made of wax that is configured to melt at a predetermined temperature. The devices are not limited to a particular type, kind or amount of meltable material. In some embodiments, the meltable material is biocompatible. The devices are not limited to a particular type, kind, or amount of first and second chemicals, so long as their mixture results in a temperature reducing chemical reaction. In some embodiments, the first material includes barium hydroxide octahydrate crystals and the second material is dry ammonium chloride. In some embodiments, the first material is water and the second material is ammonium chloride. In some embodiments, the first material is thionyl chloride ($SOCl_2$) and the second material is cobalt(II) sulfate heptahydrate. In some embodiments, the first material is water and the second material is ammonium nitrate. In some embodiments, the first material is water and the second material is potassium chloride. In some embodiments, the first material is ethanoic acid and the second material is sodium carbonate. In some embodiments, a meltable material is used that, itself, reduces heat by melting an flowing in a manner such that the heat at the outer surface of the device is reduced.

In some embodiments, the energy delivery devices prevent undesired heating and/or maintain desired energy delivery properties through adjusting the amount of energy emitted from the device (e.g., adjusting the energy wavelength resonating from the device) as temperatures increase. The devices are not limited to a particular method of adjusting the amount of energy emitted from the device. In some embodiments, the devices are configured such that as the device reaches a certain threshold temperature or as the device heats over a range, the energy wavelength resonating from the device is adjusted. The devices are not limited to a particular method for adjusting energy wavelength resonating from the device. In some embodiments, the device has therein a material that changes in volume as the temperature increases. The change in volume is used to move or adjust a component of the device that affects energy delivery. For example, in some embodiments, a material is used that expands with increasing temperature. The expansion is used to move the distal tip of the device outward (increasing its distance from the proximal end of the device), altering the energy delivery properties of the device. This finds particular use with the center-fed dipole embodiments of the present invention.

In certain embodiments, the present invention provides a device comprising an antenna configured for delivery of energy to a tissue, wherein a distal end of the antenna comprises a center-fed dipole component comprising a rigid hollow tube encompassing a conductor, wherein a stylet is secured within the hollow tube. In some embodiments, the hollow tube has a diameter equal to or less than a 20-gauge needle. In some embodiments, the hollow tube has a diameter equal to or less than a 17-gauge needle. In some embodiments, the hollow tube has a diameter equal to or less than a 12-gauge needle. In some embodiments, the device further comprises a tuning element for adjusting the amount of energy delivered to the tissue. In some embodiments, the device is configured to deliver a sufficient amount of energy to ablate the tissue or cause thrombosis. In some embodiments, the conductor extends halfway through the hollow tube. In some embodiments, the hollow tube has a length $\lambda/2$, wherein $\lambda$ is the electromagnetic field wavelength in the medium of the tissue. In some embodiments, an expandable material is positioned near the stylet such that as the device increases in temperature the expandable material expands and pushes onto the stylet moving the stylet and changes the energy delivery properties of the device. In some embodiments, the expandable material is positioned behind (proximal to) a metal disc that provides the resonant element for the center-fed dipole device. As the material expands, the disc is pushed distally, adjusting the tuning of the device. The expandable material is preferably selected so that the rate of expansion coincides with a desired change in energy delivery for optimal results. However, it should be understood that any change in the desired directions finds use with the invention. In some embodiments, the expandable material is wax.

In some embodiments, the device has a handle attached with the device, wherein the handle is configured to, for example, control the passing of coolant into and out of coolant channels. In some embodiments, only the handle is cooled. In other embodiments, the handle and an attached antenna are cooled. In some embodiments, the handle automatically passes coolant into and out of the coolant channels after a certain amount of time and/or as the device reaches a certain threshold temperature. In some embodiments, the handle automatically stops passage of coolant into and out of the coolant channels after a certain amount of time and/or as the temperature of the device drops below a certain threshold temperature. In some embodiments, coolant flowed through the handle is manually controlled.

In some embodiments, the energy delivery devices have therein a center fed dipole component (see, e.g., U.S. patent application Ser. No. 11/728,457; herein incorporated by reference in its entirety). In some embodiments, the energy delivery devices comprise a catheter with multiple segments for transmitting and emitting energy (see, e.g., U.S. patent application Ser. Nos. 11/237,430, 11/237,136, and 11/236,985; each herein incorporated by reference in their entireties). In some embodiments, the energy delivery devices comprise a triaxial microwave probe with optimized tuning capabilities to reduce reflective heat loss (see, e.g., U.S. Pat. No. 7,101,369; see, also, U.S. patent application Ser. Nos. 10/834,802, 11/236,985, 11/237,136, 11/237,430, 11/440,331, 11/452,637, 11/502,783, 11/514,628; and International Patent Application No. PCT/US05/14534; herein incorporated by reference in its entirety). In some embodiments, the energy delivery devices emit energy through a coaxial transmission line (e.g., coaxial cable) having air or other gases as a dielectric core (see, e.g., U.S. patent application Ser. No. 11/236,985; herein incorporated by reference in its entirety). In some such embodiments, materials that support the structure of the device between the inner and outer conductors may be removed prior to use. For example, in some embodiments, the materials a made of a dissolvable or meltable material that is remove prior to or during use. In some embodiments, the materials are meltable and are removed during use (upon exposure to heat) so as to optimize the energy delivery properties of the device over time (e.g., in response to temperature changes in tissue, etc.).

The present invention is not limited to a particular coaxial transmission line shape. Indeed, in some embodiments, the shape of the coaxial transmission line and/or the dielectric element is adjustable to fit a particular need. In some embodiments, the cross-sectional shape of the coaxial transmission line and/or the dielectric element is circular. In some embodiments, the cross-sectional shape is non-circular (e.g., oval, etc.). Such shapes may apply to the coaxial cable as a whole, or may apply to one or more sub-components only. For example, an oval dielectric material may be placed in a circular outer conductor. This, for example, has the advantage of creating two channels that may be employed, for example, to circulate coolant. As another example, square/rectangular dielectric material may be placed in a circular out conductor. This, for example, has the advantage of creating four channels. Different polygonal shapes in the cross-section (e.g., pentagon, hexagon, etc.) may be employed to create different numbers and shapes of channels. The cross-sectional shape need not be the same throughout the length of the cable. In some embodiments, a first shape is used for a first region (e.g., a proximal region) of the cable and a second shape is used for a second region (e.g., a distal region) of the cable. Irregular shapes may also be employed. For example, a dielectric material having an indented groove running its length may be employed in a circular outer conductor to create a single channel of any desired size and shape. In some embodiments, the channel provides space for feeding coolant, a needle, or other desired components into the device without increasing the ultimate outer diameter of the device.

Likewise, in some embodiments, an antenna of the present invention has a non-circular cross-sectional shape along its length or for one or more subsections of its length. In some embodiments, the antenna is non-cylindrical, but contains a coaxial cable that is cylindrical. In other embodiments, the antenna is non-cylindrical and contains a coaxial cable that is non-cylindrical (e.g., matching the shape of the antenna or having a different non-cylindrical shape). In some embodiments, having any one or more components (e.g., cannula, outer shell of antenna, outer conductor of coaxial cable, dielectric material of coaxial cable, inner conductor of coaxial cable) possessing a non-cylindrical shape permits the creation of one or more channels in the device that may be used, among other reasons, to circulate coolant. Non-circular shapes, particularly in the outer diameter of the antenna also find use for certain medical or other applications. For example, a shape may be chosen to maximize flexibility or access to particular inner body locations. Shape may also be chose to optimize energy delivery. Shape (e.g., non-cylindrical shape) may also be selected to maximize rigidity and/or strength of the device, particularly for small diameter devices.

In certain embodiments, the present invention provides a device comprising an antenna, wherein the antenna comprises an outer conductor enveloped around an inner conductor, wherein the inner conductor is designed to receive and transmit energy, wherein the outer conductor has therein at least one gap positioned circumferentially along the outer conductor, wherein multiple energy peaks are generated along the length of the antenna, the position of the energy peaks controlled by the location of the gap. In some embodiments, the energy is microwave energy and/or radiofrequency energy. In some embodiments, the outer conductor has therein two of the gaps. In some embodiments, the antenna comprises a dielectric layer disposed between the inner conductor and the outer conductor. In some embodiments, the dielectric layer has near-zero conductivity. In some embodiments, the device further comprises a stylet. In some embodiments, the inner conductor has a diameter of approximately 0.013 inches or less.

In some embodiments, any gaps or inconsistencies or irregularities in the outer conductor or outer surface of the device are filled with a material to provide a smooth, even, or substantially smooth, even outer surface. In some embodiments, a heat-resistant, resin is used to fill gaps, inconsistencies, and/or irregularities. In some embodiments, the resin is biocompatible. In other embodiments, it is not biocompatible, but, for example, can be coated with a biocompatible material. In some embodiments, the resin is configurable to any desired size or shape. As such, the resin, when hardened, may be used to provide a sharp stylet tip to the devices or any other desired physical shape.

In some embodiments, the device comprises a sharp stylet tip. The tip may be made of any material. In some embodiments, the tip is made from hardened resin. In some embodiments, the tip is metal. In some such embodiments, the metal tip is an extension of a metal portion of an antenna and is electrically active.

In some embodiments, the energy delivery devices are configured to delivery energy to a tissue region within a system comprising a processor, a power supply, a power splitter with the capability of individual control of power delivery to each antenna, an imaging system, a tuning system, and/or a temperature adjustment system.

The present invention is not limited to a particular type of processor. In some embodiments, the processor is designed to, for example, receive information from components of the system (e.g., temperature monitoring system, energy delivery device, tissue impedance monitoring component, etc.), display such information to a user, and manipulate (e.g., control) other components of the system. In some embodiments, the processor is configured to operate within a system comprising an energy delivery device, a power supply, a power splitter, an imaging system, a tuning system, and/or a temperature adjustment system.

The present invention is not limited to a particular type of power supply. In some embodiments, the power supply is configured to provide any desired type of energy (e.g., microwave energy, radiofrequency energy, radiation, cryo energy, electroporation, high intensity focused ultrasound, and/or mixtures thereof). In some embodiments, the power supply utilizes a power splitter to permit delivery of energy to two or more energy delivery devices. In some embodiments, the power supply is configured to operate within a system comprising a power splitter, a processor, an energy delivery device, an imaging system, a tuning system, and/or a temperature adjustment system.

The present invention is not limited to a particular type of imaging system. In some embodiments, the imaging system utilizes imaging devices (e.g., endoscopic devices, stereotactic computer assisted neurosurgical navigation devices, thermal sensor positioning systems, motion rate sensors, steering wire systems, intraprocedural ultrasound, fluoroscopy, computerized tomography magnetic resonance imaging, nuclear medicine imaging devices triangulation imaging, thermoacoustic imaging, infrared and/or laser imaging, electromagnetic imaging) (see, e.g., U.S. Pat. Nos. 6,817,976, 6,577,903, and 5,697,949, 5,603,697, and International Patent Application No. WO 06/005,579; each herein incorporated by reference in their entireties). In some embodiments, the systems utilize endoscopic cameras, imaging components, and/or navigation systems that permit or assist in placement, positioning, and/or monitoring of any of the items used with the energy systems of the present invention. In some embodiments, the imaging system is configured to provide location information of particular components of the energy delivery system (e.g., location of the energy delivery device). In some embodiments, the imaging system is configured to operate within a system comprising a processor, an energy delivery device, a power supply, a tuning system, and/or a temperature adjustment system.

The present invention is not limited to a particular tuning system. In some embodiments, the tuning system is configured to permit adjustment of variables (e.g., amount of energy delivered, frequency of energy delivered, energy delivered to one or more of a plurality of energy devices that are provided in the system, amount of or type of coolant provided, etc.) within the energy delivery system. In some embodiments, the tuning system comprises a sensor that provides feedback to the user or to a processor that monitors the function of an energy delivery device continuously or at time points. The sensor may record and/or report back any number of properties, including, but not limited to, heat at one or more positions of a components of the system, heat at the tissue, property of the tissue, and the like. The sensor may be in the form of an imaging device such as CT, ultrasound, magnetic resonance imaging, fluoroscopy, nuclear medicine imaging, or any other imaging device. In some embodiments, particularly for research application, the system records and stores the information for use in future optimization of the system generally and/or for optimization of energy delivery under particular conditions (e.g., patient type, tissue type, size and shape of target region, location of target region, etc.). In some embodiments, the tuning system is configured to operate within a system comprising a processor, an energy delivery device, a power supply, an imaging, and/or a temperature adjustment system. In some embodiments, the imaging or other control components provide feedback to the ablation device so that the power output (or other control parameter) can be adjusted to provide an optimum tissue response.

The present invention is not limited to a particular temperature adjustment system. In some embodiments, the temperature adjustment systems are designed to reduce unwanted heat of various components of the system (e.g., energy delivery devices) during medical procedures (e.g., tissue ablation) or keep the target tissue within a certain temperature range. In some embodiments, the temperature adjustment systems are configured to operate within a system comprising a processor, an energy delivery device, a power supply, a power splitter, a tuning system, and/or an imaging system.

In some embodiments, the systems further comprise temperature monitoring or reflected power monitoring systems for monitoring the temperature or reflected power of various components of the system (e.g., energy delivery devices) and/or a tissue region. In some embodiments, the monitoring systems are designed to alter (e.g., prevent, reduce) the delivery of energy to a particular tissue region if, for example, the temperature or amount of reflected energy, exceeds a predetermined value. In some embodiments, the temperature monitoring systems are designed to alter (e.g., increase, reduce, sustain) the delivery of energy to a particular tissue region so as to maintain the tissue or energy delivery device at a preferred temperature or within a preferred temperature range.

In some embodiments, the systems further comprise an identification or tracking system configured, for example, to prevent the use of previously used components (e.g., non-sterile energy delivery devices), to identify the nature of a component of the system so the other components of the system may be appropriately adjusted for compatibility or optimized function. In some embodiments, the system reads a bar code or other information-conveying element associated with a component of the systems of the invention.

The present invention is not limited by the type of components used in the systems or the uses employed. Indeed, the devices may be configured in any desired manner. Likewise, the systems and devices may be used in any application where energy is to be delivered. Such uses include any and all medical, veterinary, and research applications. However, the systems and devices of the present invention may be used in agricultural settings, manufacturing settings, mechanical settings, or any other application where energy is to be delivered.

In some embodiments, the systems are configured for percutaneous, intravascular, intracardiac, laparoscopic, or surgical delivery of energy. In some embodiments, the systems are configured for delivery of energy to a target tissue or region. The present invention is not limited by the nature of the target tissue or region. Uses include, but are not limited to, treatment of heart arrhythmia, tumor ablation (benign and malignant), control of bleeding during surgery, after trauma, for any other control of bleeding, removal of soft tissue, tissue resection and harvest, treatment of varicose veins, intraluminal tissue ablation (e.g., to treat esophageal pathologies such as Barrett's Esophagus and esophageal adenocarcinoma), treatment of bony tumors, normal bone, and benign bony conditions, intraocular uses, uses in cosmetic surgery, treatment of pathologies of the central nervous system including brain tumors and electrical disturbances, sterilization procedures (e.g., ablation of the fallopian tubes) and cauterization of blood vessels or tissue for any purposes. In some embodiments, the surgical application comprises ablation therapy (e.g., to achieve coagulative necrosis). In some embodiments, the surgical application comprises tumor ablation to target, for example, metastatic tumors. In some embodiments, the device is configured for movement and positioning, with minimal damage to the tissue or organism, at any desired location, including but not limited to, the brain, neck, chest, abdomen, and pelvis. In some embodiments, the systems are configured for guided delivery, for example, by computerized tomography, ultrasound, magnetic resonance imaging, fluoroscopy, and the like.

In certain embodiments, the present invention provides methods of treating a tissue region, comprising: providing a tissue region and a system described herein (e.g., an energy delivery device, and at least one of the following components: a processor, a power supply, a power splitter, a temperature monitor, an imager, a tuning system, and/or a temperature reduction system); positioning a portion of the energy delivery device in the vicinity of the tissue region, and delivering an amount of energy with the device to the tissue region. In some embodiments, the tissue region is a tumor. In some embodiments, the delivering of the energy results in, for example, the ablation of the tissue region and/or thrombosis of a blood vessel, and/or electroporation of a tissue region. In some embodiments, the tissue region is a tumor. In some embodiments, the tissue region comprises one or more of the heart, liver, genitalia, stomach, lung, large intestine, small intestine, brain, neck, bone, kidney, muscle, tendon, blood vessel, prostate, bladder, and spinal cord. In some embodiments, the processor receives information from sensors and monitors and controls the other components of the systems. In some embodiments, the energy output of the power supply is altered, as desired, for optimized therapy. In some embodiments, where more than one energy delivery component is provided, the amount of energy delivered to each of the delivery components is optimized to achieve the desired result. In some embodiments, the temperature of the system is monitored by a temperature sensor and, upon reaching or approaching a threshold level, is reduced by activation of the temperature reduction system. In some embodiments the imaging system provides information to the processor, which is displayed to a user of the system and may be used in a feedback loop to control the output of the system.

In some embodiments, energy is delivered to the tissue region in different intensities and from different locations within the device. For example, certain regions of the tissue region may be treated through one portion of the device, while other regions of the tissue may be treated through a different portion of the device. In addition, two or more regions of the device may simultaneously deliver energy to a particular tissue region so as to achieve constructive phase interference (e.g., wherein the emitted energy achieves a synergistic effect). In other embodiments, two or more regions of the device may deliver energy so as to achieve a destructive interference effect. In some embodiments, the method further provides additional devices for purposes of achieving constructive phase interference and/or destructive phase interference. In some embodiments, phase interference (e.g., constructive phase interference, destructive phase interference), between one or more devices, is controlled by a processor, a tuning element, a user, and/or a power splitter.

The systems, devices, and methods of the present invention may be used in conjunction with other systems, device, and methods. For example, the systems, devices, and methods of the present invention may be used with other ablation devices, other medical devices, diagnostic methods and reagents, imaging methods and reagents, and therapeutic methods and agents. Use may be concurrent or may occur before or after another intervention. The present invention contemplates the use systems, devices, and methods of the present invention in conjunction with any other medical interventions.

Additionally, integrated ablation and imaging systems are needed that provide feedback to a user and permit communication between various system components. System parameters may be adjusted during the ablation to optimize energy delivery. In addition, the user is able to more accurately determine when the procedure is successfully completed, reducing the likelihood of unsuccessful treatments and/or treatment related complications.

DETAILED DESCRIPTION

Figure 1:
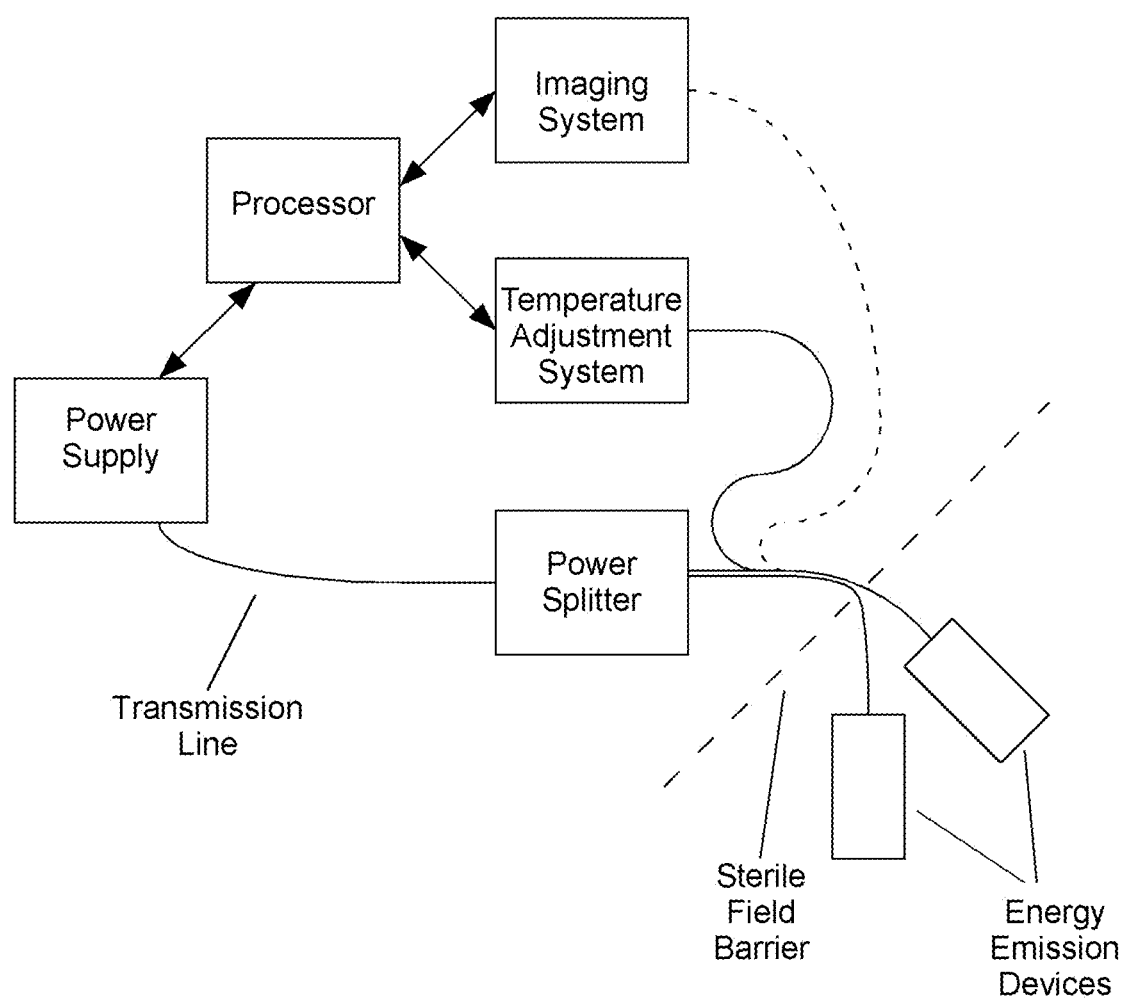
FIG. 1 shows a schematic view of an energy delivery system in an embodiment of the invention.

The present invention relates to comprehensive systems, devices and methods for delivering energy (e.g., microwave energy, radiofrequency energy) to tissue for a wide variety of applications, including medical procedures (e.g., tissue ablation, resection, cautery, vascular thrombosis, intraluminal ablation of a hollow viscus, cardiac ablation for treatment of arrhythmias, electrosurgery, tissue harvest, cosmetic surgery, intraocular use, etc.). In particular, the present invention provides systems for the delivery of microwave energy comprising a power supply, a power splitter, a processor, an energy emitting device, a cooling system, an imaging system, a temperature monitoring system, and/or a tracking system. In certain embodiments, systems, devices, and methods are provided for treating a tissue region (e.g., a tumor) through use of the energy delivery systems of the present invention.

The systems of the present invention may be combined within various system/kit embodiments. For example, the present invention provides systems comprising one or more of a generator, a power distribution system, a power splitter, an energy applicator, along with any one or more accessory component (e.g., surgical instruments, software for assisting in procedure, processors, temperature monitoring devices, etc.). The present invention is not limited to any particular accessory component.

The systems of the present invention may be used in any medical procedure (e.g., percutaneous or surgical) involving delivery of energy (e.g., radiofrequency energy, microwave energy, laser, focused ultrasound, etc.) to a tissue region. The systems are not limited to treating a particular type or kind of tissue region (e.g., brain, liver, heart, blood vessels, foot, lung, bone, etc.). For example, the systems of the present invention find use in ablating tumor regions. Additional treatments include, but are not limited to, treatment of heart arrhythmia, tumor ablation (benign and malignant), control of bleeding during surgery, after trauma, for any other control of bleeding, removal of soft tissue, tissue resection and harvest, treatment of varicose veins, intraluminal tissue ablation (e.g., to treat esophageal pathologies such as Barrett's Esophagus and esophageal adenocarcinoma), treatment of bony tumors, normal bone, and benign bony conditions, intraocular uses, uses in cosmetic surgery, treatment of pathologies of the central nervous system including brain tumors and electrical disturbances, sterilization procedures (e.g., ablation of the fallopian tubes) and cauterization of blood vessels or tissue for any purposes. In some embodiments, the surgical application comprises ablation therapy (e.g., to achieve coagulative necrosis). In some embodiments, the surgical application comprises tumor ablation to target, for example, primary or metastatic tumors. In some embodiments, the surgical application comprises the control of hemorrhage (e.g. electrocautery). In some embodiments, the surgical application comprises tissue cutting or removal. In some embodiments, the device is configured for movement and positioning, with minimal damage to the tissue or organism, at any desired location, including but not limited to, the brain, neck, chest, abdomen, pelvis, and extremities. In some embodiments, the device is configured for guided delivery, for example, by computerized tomography, ultrasound, magnetic resonance imaging, fluoroscopy, and the like.

The illustrated embodiments provided below describe the systems of the present invention in terms of medical applications (e.g., ablation of tissue through delivery of microwave energy). However, it should be appreciated that the systems of the present invention are not limited to medical applications. The systems may be used in any setting requiring delivery of energy to a load (e.g., agricultural settings, manufacture settings, research settings, etc.). The illustrated embodiments describe the systems of the present invention in terms of microwave energy. It should be appreciated that the systems of the present invention are not limited to a particular type of energy (e.g., radiofrequency energy, microwave energy, focused ultrasound energy, laser, plasma).

The systems of the present invention are not limited to any particular component or number of components. In some embodiments, the systems of the present invention include, but are not limited to including, a power supply, a power splitter, a processor, an energy delivery device with an antenna, a cooling system, an imaging system, and/or a tracking system. When multiple antennas are in use, the system may be used to individually control each antenna separately.

FIG. 1 shows an exemplary system of the invention. As shown, the energy delivery system comprises a power supply, a transmission line, a power distribution component (e.g., power splitter), a processor, an imaging system, a temperature monitoring system and an energy delivery device. In some embodiments, as shown, the components of the energy delivery systems are connected via a transmission line, cables, etc. In some embodiments, the energy delivery device is separated from the power supply, power splitter, processor, imaging system, temperature monitoring system across a sterile field barrier.

Exemplary components of the energy delivery systems are described in more detail in the following sections: I. Power Supply; II. Energy delivery devices; III. Processor; IV. Imaging Systems; V. Tuning Systems; VI. Temperature Adjustment Systems; VII. Identification Systems; VIII. Temperature Monitoring Devices; and IX. Uses.

I. Power Supply

The energy utilized within the energy delivery systems of the present invention is supplied through a power supply. The present invention is not limited to a particular type or kind of power supply. In some embodiments, the power supply is configured to provide energy to one or more components of the energy delivery systems of the present invention (e.g., ablation devices). The power supply is not limited to providing a particular type of energy (e.g., radiofrequency energy, microwave energy, radiation energy, laser, focused ultrasound, etc.). The power supply is not limited to providing particular amounts of energy or at a particular rate of delivery. In some embodiments, the power supply is configured to provide energy to an energy delivery device for purposes of tissue ablation.

The present invention is not limited to a particular type of power supply. In some embodiments, the power supply is configured to provide any desired type of energy (e.g., microwave energy, radiofrequency energy, radiation, cryo energy, electroporation, high intensity focused ultrasound, and/or mixtures thereof). In some embodiments, the type of energy provided with the power supply is microwave energy. In some some embodiments, the power supply provides microwave energy to ablation devices for purposes of tissue ablation. The use of microwave energy in the ablation of tissue has numerous advantages. For example, microwaves have a broad field of power density (e.g., approximately 2 cm surrounding an antenna depending on the wavelength of the applied energy) with a correspondingly large zone of active heating, thereby allowing uniform tissue ablation both within a targeted zone and in perivascular regions (see, e.g., International Publication No. WO 2006/004585; herein incorporated by reference in its entirety). In addition, microwave energy has the ability to ablate large or multiple zones of tissue using multiple probes with more rapid tissue heating. Microwave energy has an ability to penetrate tissue to create deep lesions with less surface heating. Energy delivery times are shorter than with radiofrequency energy and probes can heat tissue sufficiently to create an even and symmetrical lesion of predictable and controllable depth. Microwave energy is generally safe when used near vessels. Also, microwaves do not rely on electrical conduction as it radiates through tissue, fluid/blood, as well as air. Therefore, microwave energy can be used in tissue, lumens, lungs, and intravascularly.

In some embodiments, the power supply is an energy generator. In some embodiments, the generator is configured to provide as much as 100 watts of microwave power of a frequency of from 915 MHz to 2.45 GHz, although the present invention is not so limited. Solid state microwave generators in the 1-3 GHz range are very expensive. Therefore, in some embodiments, a conventional magnetron of the type commonly used in microwave ovens is chosen as the generator. It should be appreciated, however, that any other suitable microwave power source can substituted in its place. In some embodiments, the types of generators include, but are not limited to, those available from Cober-Muegge, LLC, Norwalk, Conn., USA, Sairem generators, and Gerling Applied Engineering generators. In some embodiments, the generator has at least approximately 60 Watts available (e.g., 50, 55, 56, 57, 58, 59, 60, 61, 62, 65, 70, 100, 500, 1000 Watts). For a higher-power operation, the generator is able to provide approximately 300 Watts (e.g., 200 Watts, 280, 290, 300, 310, 320, 350, 400, 750 Watts). In some embodiments, wherein multiple antennas are used, the generator is able to provide as much energy as necessary (e.g., 400 Watts, 500, 750, 1000, 2000, 10,000 Watts).

In some embodiments, the power supply distributes energy (e.g., collected from a generator) with a power distribution system. The present invention is not limited to a particular power distribution system. In some embodiments, the power distribution system is configured to provide energy to an energy delivery device (e.g., a tissue ablation catheter) for purposes of tissue ablation. The power distribution system is not limited to a particular manner of collecting energy from, for example, a generator. The power distribution system is not limited to a particular manner of providing energy to ablation devices. In some embodiments, the power distribution system is configured to transform the characteristic impedance of the generator such that it matches the characteristic impedance of an energy delivery device (e.g., a tissue ablation catheter).

In some embodiments, the power distribution system is configured with a variable power splitter so as to provide varying energy levels to different regions of an energy delivery device or to different energy delivery devices (e.g., a tissue ablation catheter). In some embodiments, the power splitter is provided as a separate component of the system. In some embodiments, the power splitter is used to feed multiple energy delivery devices with separate energy signals. In some embodiments, the power splitter electrically isolates the energy delivered to each energy delivery device so that, for example, if one of the devices experiences an increased load as a result of increased temperature deflection, the energy delivered to that unit is altered (e.g., reduced, stopped) while the energy delivered to alternate devices is unchanged. The present invention is not limited to a particular type or kind of power splitter. In some embodiments, the power splitter is designed by SM Electronics. In some embodiments, the power splitter is configured to receive energy from a power generator and provide energy to additional system components (e.g., energy delivery devices). In some embodiments the power splitter is able to connect with one or more additional system components (e.g., 1, 2, 3, 4, 5, 7, 10, 15, 20, 25, 50, 100, 500 . . . ). In some embodiments, the power splitter is configured to deliver variable amounts of energy to different regions within an energy delivery device for purposes of delivering variable amounts of energy from different regions of the device. In some embodiments, the power splitter is used to provide variable amounts of energy to multiple energy delivery devices for purposes of treating a tissue region. In some embodiments, the power splitter is configured to operate within a system comprising a processor, an energy delivery device, a temperature adjustment system, a power splitter, a tuning system, and/or an imaging system. In some embodiments, the power splitter is able to handle maximum generator outputs plus, for example, 25% (e.g., 20%, 30%, 50%). In some embodiments, the power splitter is a 1000-watt-rated 2-4 channel power splitter.

In some embodiments, where multiple antennas are employed, the system of the present invention may be configured to run them simultaneously or sequentially (e.g., with switching). In some embodiments, the system is configured to phase the fields for constructive or destructive interference. Phasing may also be applied to different elements within a single antenna.

II. Energy Delivery Devices

The energy delivery systems of the present invention contemplate the use of any type of device configured to deliver (e.g., emit) energy (e.g., ablation device, surgical device, etc.) (see, e.g., U.S. Pat. Nos. 7,101,369, 7,033,352, 6,893,436, 6,878,147, 6,823,218, 6,817,999, 6,635,055, 6,471,696, 6,383,182, 6,312,427, 6,287,302, 6,277,113, 6,251,128, 6,245,062, 6,026,331, 6,016,811, 5,810,803, 5,800,494, 5,788,692, 5,405,346, 4,494,539, U.S. patent application Ser. Nos. 11/728,460, 11/728,457, 11/728,428, 11/237,136, 11/236,985, 10/980,699, 10/961,994, 10/961,761, 10/834,802, 10/370,179, 09/847,181; Great Britain Patent Application Nos. 2,406,521, 2,388,039; European Patent No. 1395190; and International Patent Application Nos. WO 06/008481, WO 06/002943, WO 05/034783, WO 04/112628, WO 04/033039, WO 04/026122, WO 03/088858, WO 03/039385 WO 95/04385; each herein incorporated by reference in their entireties). Such devices include any and all medical, veterinary, and research applications devices configured for energy emission, as well as devices used in agricultural settings, manufacturing settings, mechanical settings, or any other application where energy is to be delivered.

In some embodiments, the systems utilize energy delivery devices having therein antennae configured to emit energy (e.g., microwave energy, radiofrequency energy, radiation energy). The systems are not limited to particular types or designs of antennae (e.g., ablation device, surgical device, etc.). In some embodiments, the systems utilize energy delivery devices having linearly shaped antennae (see, e.g., U.S. Pat. Nos. 6,878,147, 4,494,539, U.S. patent application Ser. Nos. 11/728,460, 11/728,457, 11/728,428, 10/961,994, 10/961,761; and International Patent Application No., WO 03/039385; each herein incorporated by reference in their entireties). In some embodiments, the systems utilize energy delivery devices having non-linearly shaped antennae (see, e.g., U.S. Pat. Nos. 6,251,128, 6,016,811, and 5,800,494, U.S. patent application Ser. No. 09/847,181, and International Patent Application No. WO 03/088858; each herein incorporated by reference in their entireties). In some embodiments, the antennae have horn reflection components (see, e.g., U.S. Pat. Nos. 6,527,768, 6,287,302; each herein incorporated by reference in their entireties). In some embodiments, the antenna has a directional reflection shield (see, e.g., U.S. Pat. No. 6,312,427; herein incorporated by reference in its entirety). In some embodiments, the antenna has therein a securing component so as to secure the energy delivery device within a particular tissue region (see, e.g., U.S. Pat. Nos. 6,364,876, and 5,741,249; each herein incorporated by reference in their entireties).

Generally, antennae configured to emit energy comprise coaxial transmission lines. The devices are not limited to particular configurations of coaxial transmission lines. Examples of coaxial transmission lines include, but are not limited to, coaxial transmission lines developed by Pasternack, Micro-coax, and SRC Cables. In some embodiments, the coaxial transmission line has a center conductor, a dielectric element, and an outer conductor (e.g., outer shield). In some embodiments, the systems utilize antennae having flexible coaxial transmission lines (e.g., for purposes of positioning around, for example, pulmonary veins or through tubular structures) (see, e.g., U.S. Pat. Nos. 7,033, 352, 6,893,436, 6,817,999, 6,251,128, 5,810,803, 5,800, 494; each herein incorporated by reference in their entireties). In some embodiments, the systems utilize antennae having rigid coaxial transmission lines (see, e.g., U.S. Pat. No. 6,878,147, U.S. patent application Ser. Nos. 10/961,994, 10/961,761, and International Patent Application No. WO 03/039385; each herein incorporated by reference in their entireties).

Figure 2:
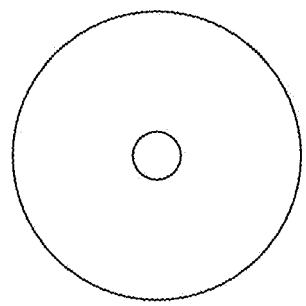
FIG. 2 shows various shapes of coaxial transmission lines and/or the dielectric elements in some embodiments of the present invention.
Figure 2:
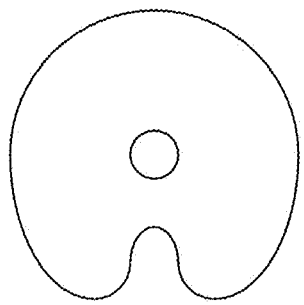
Figure 2:
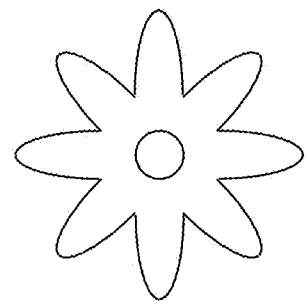
Figure 2:
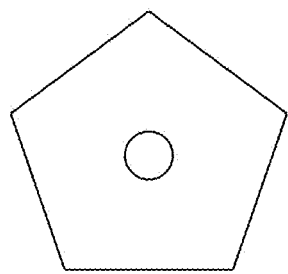
Figure 2:
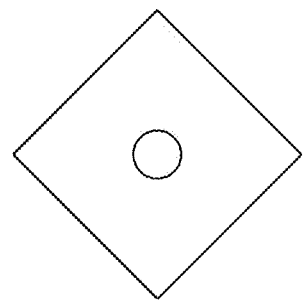
Figure 2:
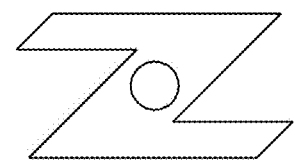
Figure 2:
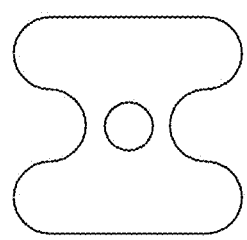
Figure 2:
Figure 2:
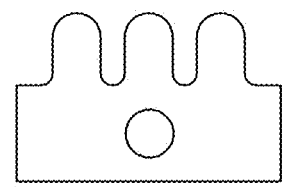

The present invention is not limited to a particular coaxial transmission line shape. Indeed, in some embodiments, the shape of the coaxial transmission line and/or the dielectric element is selected and/or adjustable to fit a particular need. FIG. 2 shows some of the various, non-limiting shapes the coaxial transmission line and/or the dielectric element may assume.

In some embodiments, the outer conductor is a 20-gauge needle or a component of similar diameter to a 20-gauge needle. Preferably, for percutaneous use the outer conductor is not larger than a 16-gauge needle (e.g., no larger than an 18-gauge needle). In some embodiments, the outer conductor is a 17-gauge needle. However, in some embodiments, larger devices are used, as desired. For example, in some embodiments, a 12-gauge diameter is used. The present invention is not limited by the size of the outer conductor. In some embodiments, the outer conductor is configured to fit within series of larger needles for purposes of assisting in medical procedures (e.g., assisting in tissue biopsy) (see, e.g., U.S. Pat. Nos. 6,652,520, 6,582,486, 6,355,033, 6,306, 132; each herein incorporated by reference in their entireties). In some embodiments, the center conductor is configured to extend beyond the outer conductor for purposes of delivering energy to a desired location. In some embodiments, some or all of the feedline characteristic impedance is optimized for minimum power dissipation, irrespective of the type of antenna that terminates at its distal end.

In some embodiments, the energy delivery devices are provided with a proximal portion and a distal portion, wherein the distal portion is detachable and provided in a variety of different configurations that can attach to a core proximal portion. For example, in some embodiments, the proximal portion comprises a handle and an interface to other components of the system (e.g., power supply) and the distal portion comprises a detachable antenna having desired properties. A plurality of different antenna configured for different uses may be provided and attached to the handle unit for the appropriate indication.

In some embodiments, the device is configured to attach with a detachable handle. The present invention is not limited to a particular type of detachable handle. In some embodiments, the detachable handle is configured to connect with multiple devices (e.g., 1, 2, 3, 4, 5, 10, 20, 50 . . . ) for purposes of controlling the energy delivery through such devices.

In some embodiments, the device is designed to physically surround a particular tissue region for purposes of energy delivery (e.g., the device may be flexibly shaped around a particular tissue region). For example, in some embodiments, the device may be flexibly shaped around a blood vessel (e.g., pulmonary vein) for purposes of delivering energy to a precise region within the tissue.

In some embodiments, the energy delivery device is provided as two or more separate antenna attached to the same or different power supplies. In some embodiments, the different antenna are attached to the same handle, while in other embodiments different handles are provided for each antenna. In some embodiments, multiple antennae are used within a patient simultaneously or in series (e.g., switching) to deliver energy of a desired intensity and geometry within the patient. In some embodiments, the antennas are individually controllable. In some embodiments, the multiple antennas may be operated by a single user, by a computer, or by multiple users.

In some embodiments, the energy delivery devices are designed to operate within a sterile field. The present invention is not limited to a particular sterile field setting. In some embodiments, the sterile field includes a region surrounding a subject (e.g., an operating table). In some embodiments, the sterile field includes any region permitting access only to sterilized items (e.g., sterilized devices, sterilized accessory agents, sterilized body parts). In some embodiments, the sterile field includes any region vulnerable to pathogen infection. In some embodiments, the sterile field has therein a sterile field barrier establishing a barrier between a sterile field and a non-sterile field. The present invention is not limited to a particular sterile field barrier. In some embodiments, the sterile field barrier is the drapes surrounding a subject undergoing a procedure involving the systems of the present invention (e.g., tissue ablation). In some embodiments, a room is sterile and provides the sterile field. In some embodiments, the sterile field barrier is established by a user of the systems of the present invention (e.g., a physician). In some embodiments, the sterile field barrier hinders entry of non-sterile items into the sterile field. In some embodiments, the energy delivery device is provided in the sterile field, while one or more other components of the system (e.g., the power supply) are not contained in the sterile field.

In some embodiments, the energy delivery devices have therein protection sensors designed to prevent undesired use of the energy delivery devices. The energy delivery devices are not limited to a particular type or kind of protection sensors. In some embodiments, the energy delivery devices have therein a temperature sensor designed to measure the temperature of, for example, the energy delivery device and/or the tissue contacting the energy delivery device. In some embodiments, as a temperature reaches a certain level the sensor communicates a warning to a user via, for example, the processor. In some embodiments, the energy delivery devices have therein a skin contact sensor designed detect contact of the energy delivery device with skin (e.g., an exterior surface of the skin). In some embodiments, upon contact with undesired skin, the skin contact sensor communicates a warning to a user via, for example, the processor. In some embodiments, the energy delivery devices have therein an air contact sensor designed detect contact of the energy delivery device with ambient air (e.g., detection through measurement of reflective power of electricity passing through the device). In some embodiments, upon contact with undesired air, the skin contact sensor communicates a warning to a user via, for example, the processor. In some embodiments, the sensors are designed to prevent use of the energy delivery device (e.g., by automatically reducing or preventing power delivery) upon detection of an undesired occurrence (e.g., contact with skin, contact with air, undesired temperature increase/decrease). In some embodiments, the sensors communicate with the processor such that the processor displays a notification (e.g., a green light) in the absence of an undesired occurrence. In some embodiments, the sensors communicate with the processor such that the processor displays a notification (e.g., a red light) in the presence of an undesired occurrence and identifies the undesired occurrence.

In some embodiments, the energy delivery devices are used above a manufacturer's recommended power rating. In some embodiments, cooling techniques described herein are applied to permit higher power delivery. The present invention is not limited to a particular amount of power increase. In some embodiments, power ratings exceed manufacturer's recommendation by 5× or more (e.g., 5×, 6×, 10×, 15×, 20×, etc.).

In addition, the devices of the present invention are configured to deliver energy from different regions of the device (e.g., outer conductor segment gaps, described in more detail below) at different times (e.g., controlled by a user) and at different energy intensities (e.g., controlled by a user). Such control over the device permits the phasing of energy delivery fields for purposes of achieving constructive phase interference at a particular tissue region or destructive phase interference at a particular tissue region. For example, a user may employ energy delivery through two (or more) closely positioned outer conductor segments so as to achieve a combined energy intensity (e.g., constructive phase interference). Such a combined energy intensity may be useful in particularly deep or dense tissue regions. In addition, such a combined energy intensity may be achieved through utilization of two (or more) devices. In some embodiments, phase interference (e.g., constructive phase interference, destructive phase interference), between one or more devices, is controlled by a processor, a tuning element, a user, and/or a power splitter. Thus, the user is able to control the release of energy through different regions of the device and control the amount of energy delivered through each region of the device for purposes of precisely sculpting an ablation zone.

In some embodiments, the energy delivery systems of the present invention utilize energy delivery devices with optimized characteristic impedance, energy delivery devices having cooling passage channels, energy delivery devices with a center fed dipole, and energy delivery devices having a linear array of antennae components (each described in more detail above and below).

Figure 3A:
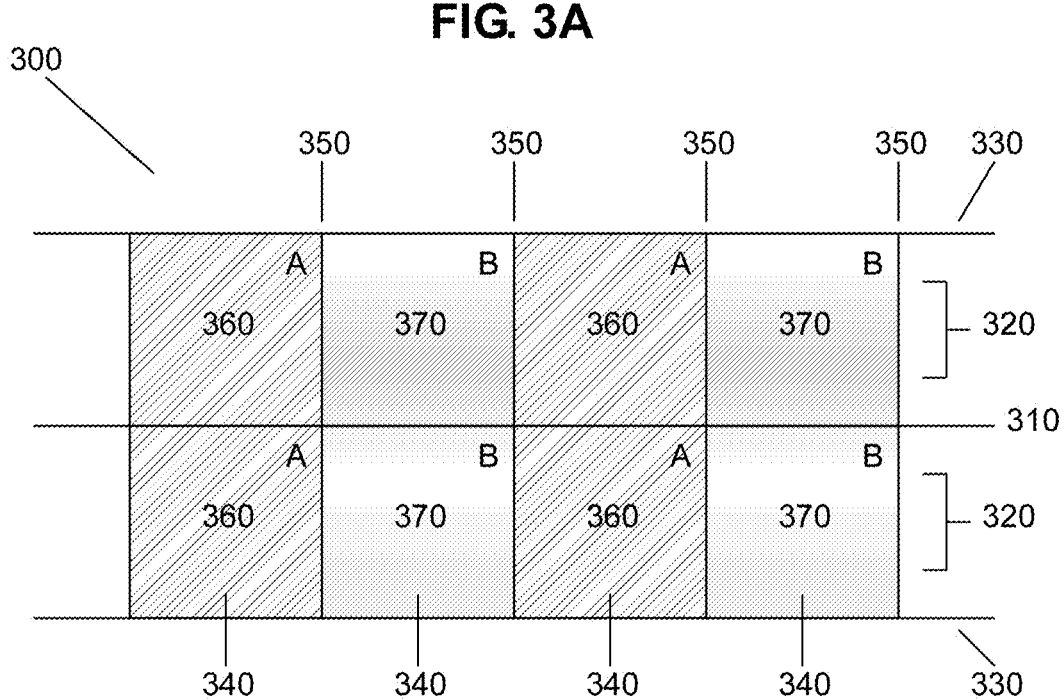
FIGS. 3A and 3B display a coaxial transmission line embodiment having partitioned segments with first and second materials blocked by meltable walls for purposes of preventing undesired device heating (e.g., heating along the outer conductor).
Figure 3B:
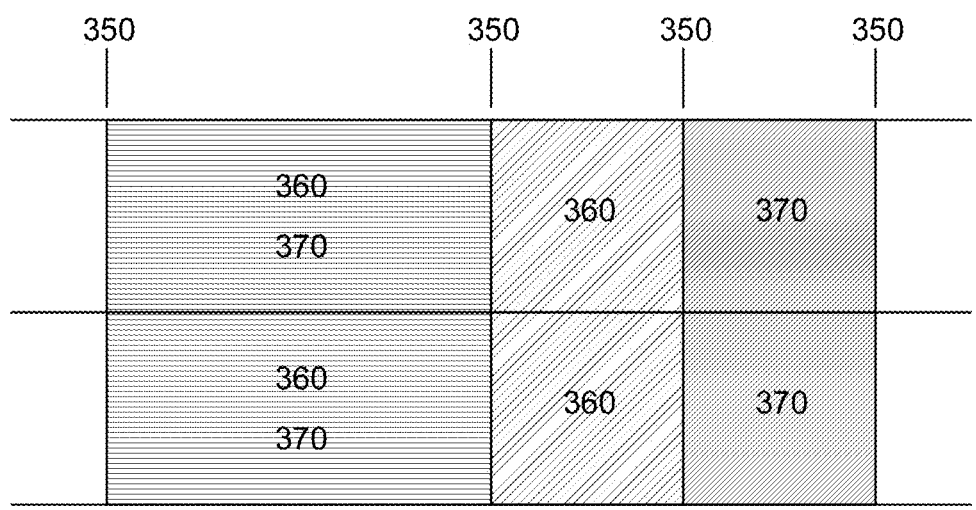

As described in the Summary of the Invention, above, the present invention provides a wide variety of methods for cooling the devices. Some embodiments employ meltable barriers that, upon melting, permit the contact of chemicals that carry out an endothermic reaction. An example of such an embodiment is shown in FIG. 3. FIGS. 3A and 3B display a region of a coaxial transmission line (e.g., a channel) having partitioned segments with first and second materials blocked by meltable walls for purposes of preventing undesired device heating (e.g., heating along the outer conductor). FIGS. 3A and 3B depict a standard coaxial transmission line 300 configured for use within any of the energy delivery devices of the present invention. As shown in FIG. 3A, the coaxial transmission line 300 has a center conductor 310, a dielectric material 320, and an outer conductor 330. In addition, the coaxial transmission line 300 has therein four partitioned segments 340 segregated by walls 350 (e.g., meltable wax walls). The partitioned segments 340 are divided into first partitioned segments 360 and second partitioned segments 370. In some embodiments, as shown in FIG. 3A, the first partitioned segments 360 and second partitioned segments 370 are successively staggered. As shown in FIG. 3A, the first partitioned segments 360 contain a first material (shading type one) and the second partitioned segments 370 contain a second material (shading type two). The walls 350 prevent the first material and second material from mixing. FIG. 3B shows the coaxial transmission line 300 described in FIG. 3A following an event (e.g., a temperature increase at one of the partitioned segments 340). As shown, one of the walls 350 has melted thereby permitting mixing of the first material contained in a region 360 and second material contained in a region 370. FIG. 3B further shows non-melted walls 350 where the temperature increase did not rise above a certain temperature threshold.

Figure 4A:
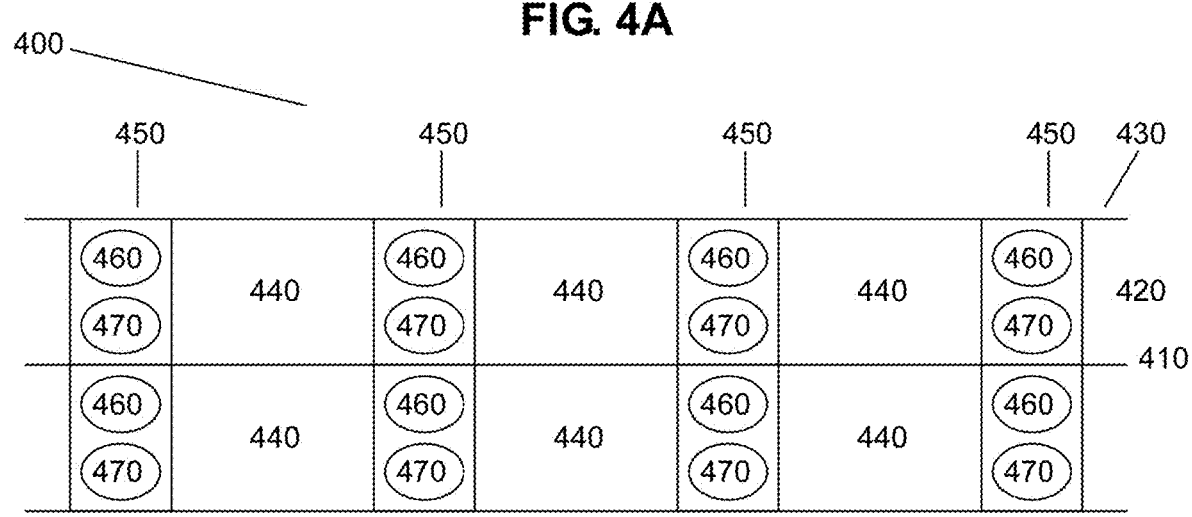
FIGS. 4A and 4B display a coaxial transmission line embodiment having partitioned segments segregated by meltable walls containing first and second materials (e.g., materials configured to generate a temperature reducing chemical reaction upon mixing) preventing undesired device heating (e.g., heating along the outer conductor).
Figure 4B:
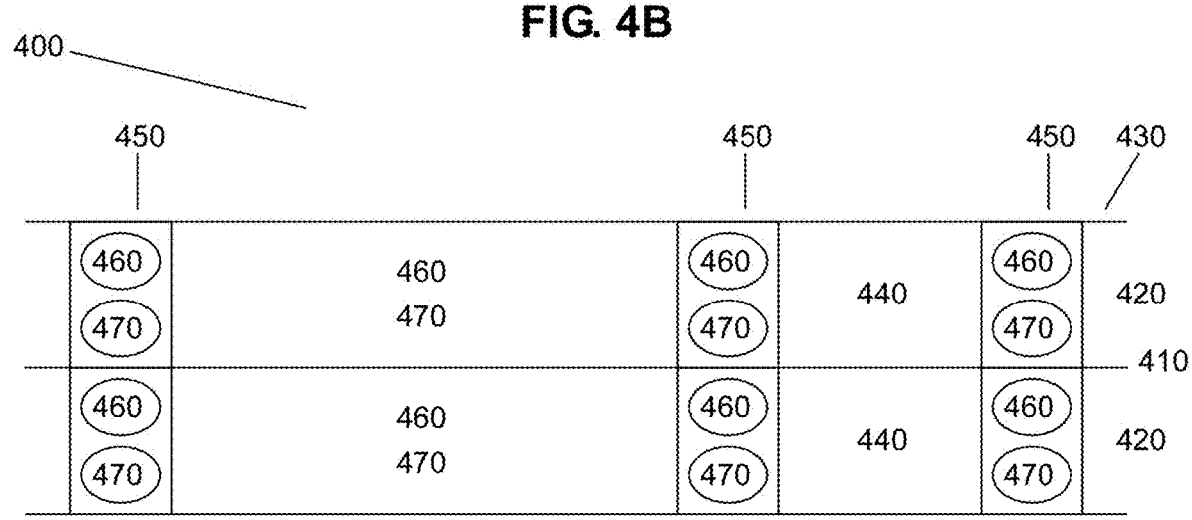

FIG. 4 shows an alternative embodiment. FIGS. 4A and 4B display a coaxial transmission line embodiment having partitioned segments segregated by meltable walls containing first and second materials (e.g., materials configured to generate a temperature reducing chemical reaction upon mixing) preventing undesired device heating (e.g., heating along the outer conductor). FIGS. 4A and 4B show a coaxial transmission line 400 configured for use within any of the energy delivery devices of the present invention. As shown in FIG. 4A, the coaxial transmission line 400 has a center conductor 410, a dielectric material 420, and an outer conductor 430. In addition, the coaxial transmission line 400 has therein four partitioned segments 440 segregated by walls 450. The walls 450 each contain a first material 460 separated from a second material 470. FIG. 4B shows the coaxial transmission line 400 described in FIG. 4A following an event (e.g., a temperature increase at one of the partitioned segments 440). As shown, one of the walls 450 has melted thereby permitting mixing of the first material 460 and second material 470 within the adjacent partitioned segments 440. FIG. 4B further demonstrates non-melted walls 450 where the temperature increase did not rise above a certain temperature threshold.

In some embodiments, the device further comprises an anchoring element for securing the antenna at a particular tissue region. The device is not limited to a particular type of anchoring element. In some embodiments, the anchoring element is an inflatable balloon (e.g., wherein inflation of the balloon secures the antenna at a particular tissue region). An additional advantage of utilizing an inflatable balloon as an anchoring element is the inhibition of blood flow or air flow to a particular region upon inflation of the balloon. Such air or blood flow inhibition is particularly useful in, for example, cardiac ablation procedures and ablation procedures involving lung tissue, vascular tissue, and gastrointestinal tissue. In some embodiments, the anchoring element is an extension of the antenna designed to engage (e.g., latch onto) a particular tissue region. Further examples include, but are not limited to, the anchoring elements described in U.S. Pat. Nos. 6,364,876, and 5,741,249; each herein incorporated by reference in their entireties.

Thus, in some embodiments, the devices of the present invention are used in the ablation of a tissue region having high amounts of air and/or blood flow (e.g., lung tissue, cardiac tissue, gastrointestinal tissue, vascular tissue). In some embodiments involving ablation of tissue regions having high amounts of air and/or blood flow, an element is further utilized for inhibiting the air and/or blood flow to that tissue region. The present invention is not limited to a particular air and/or blood flow inhibition element. In some embodiments, the device is combined with an endotracheal/endobronchial tube. In some embodiments, a balloon attached with the device may be inflated at the tissue region for purposes of securing the device(s) within the desired tissue region, and inhibiting blood and/or air flow to the desired tissue region.

Thus, in some embodiments, the systems, devices, and methods of the present invention provide an ablation device coupled with a component that provides occlusion of a passageway (e.g., bronchial occlusion). The occlusion component (e.g., inflatable balloon) may be directly mounted on the ablation system or may be used in combination with another component (e.g., an endotracheal or endobronchial tube) associated with the system.

In some embodiments, the devices of the present invention may be mounted onto additional medical procedure devices. For example, the devices may be mounted onto endoscopes, intravascular catheters, or laproscopes. In some embodiments, the devices are mounted onto steerable catheters. In some embodiments, a flexible catheter is mounted on an endoscope, intravascular catheter or laparoscope. For example, the flexible catheter, in some embodiments, has multiple joints (e.g., like a centipede) that permits bending and steering as desired to navigate to the desired location for treatment.

Energy Delivery Devices with Optimized Characteristic Impedance

In some embodiments, the energy delivery systems of the present invention utilize devices configured for delivery of microwave energy with an optimized characteristic impedance (see, e.g., U.S. patent application Ser. No. 11/728,428; herein incorporated by reference in its entirety). Such devices are configured to operate with a characteristic impedance higher than 50Ω (e.g., between 50 and 90Ω; e.g., higher than 50, . . . , 55, 56, 57, 58, 59, 60, 61, 62, . . . 90Ω, preferably at 77Ω).

Energy delivery devices configured to operate with optimized characteristic impedance are particularly useful in terms of tissue ablation procedures, and provide numerous advantages over non-optimized devices. For example, a major drawback with currently available medical devices that utilize microwave energy is the undesired dissipation of the energy through transmission lines onto a subject's tissue resulting in undesired burning. Such microwave energy loss results from limitations within the design of currently available medical devices. Standard impedance for coaxial transmission lines within medical devices is 50Ω or lower. Generally, coaxial transmission lines with impedance lower than 50Ω have high amounts of heat loss due to the presence of dielectric materials with finite conductivity values. As such, medical devices with coaxial transmission lines with impedance at 50Ω or lower have high amounts of heat loss along the transmission lines. In particular, medical devices utilizing microwave energy transmit energy through coaxial cables having therein a dielectric material (e.g., polyfluorothetraethylene or PTFE) surrounding an inner conductor. Dielectric materials such as PTFE have a finite conductivity, which result in the undesired heating of transmission lines. This is particularly true when one supplies the necessary amounts of energy for a sufficient period of time to enable tissue ablation. Energy delivery devices configured to operate with optimized characteristic impedance overcome this limitation by lacking, or substantially lacking, a solid dielectric insulator. For example, using air in place of a traditional dielectric insulator results in an efficient device operating at 77Ω. In some embodiments, the devices employ a near-zero conductivity dielectric material (e.g., air, water, inert gases, vacuum, partial vacuum, or combinations thereof). The overall temperature of the transmission lines within such devices are greatly reduced through use of coaxial transmission lines with near-zero conductivity dielectric materials, and therefore, greatly reduce undesired tissue heating.

In addition, by providing a coaxial transmission line with a dielectric material having near-zero conductivity, and avoiding the use of typical dielectric polymers, the coaxial transmission line may be designed such that it can fit within small needles (e.g., 18-20 gauge needles). Typically, medical devices configured to delivery microwave energy are designed to fit within large needles due to bulky dielectric materials. Microwave ablation has not been extensively applied clinically due to the large probe size (14 gauge) and relatively small zone of necrosis (1.6 cm in diameter) (Seki T et al., Cancer 74:817 (1994)) that is created by the only commercial device (Microtaze, Nippon Shoji, Osaka, Japan. 2.450 MHz, 1.6 mm diameter probe, 70 W for 60 seconds). Other devices use a cooling external water jacket that also increases probe size and can increase tissue damage. These large probe sizes increase the risk of complications when used in the chest and abdomen.

Energy Delivery Devices Having Coolant Passage Channels

In some embodiments, the energy delivery systems of the present invention utilize energy delivery devices having coolant passage channels (see, e.g., U.S. Pat. No. 6,461,351, and U.S. patent application Ser. No. 11/728,460; herein incorporated by reference in its entirety). In particular, the energy delivery systems of the present invention utilize devices with coaxial transmission lines that allow cooling by flowing a cooling material through the dielectric and/or the inner or outer conductor of the coaxial component. In some embodiments, the devices are configured to minimize the diameter of the device, while permitting the passage of the coolant. This is accomplished, in some embodiments, by replacing strips of the inner or outer conductor and/or solid dielectric material with channels through which a coolant is transferred. In some embodiments, the channels are generated by stripping the outer or inner conductor and/or solid dielectric material along the length of the coaxial cable from one or more (e.g., two, three, four) zones. With the removed portions of the outer or inner conductor and/or solid dielectric material creating channels for transfer of the coolant, the stripped component fits within a smaller outer conductor than it did prior to removal of the outer or inner conductor and/or solid dielectric material. This provides for smaller devices with all of the advantages derived therefrom. In some embodiments where multiple channels are employed, coolant transfer may be in alternative directions through one or more of the channels. An advantage of such devices is that the diameter of the coaxial cable does not need to be increased to accommodate coolant. This permits the use of cooled devices that are minimally invasive and permit access to regions of a body that are otherwise inaccessible or accessible only with undesired risk. The use of coolant also permits greater energy delivery and/or energy deliver for prolonged periods of time. Additional cooling embodiments are described above in the Summary of the Invention.

In some embodiments, the device has a handle attached with the device, wherein the handle is configured to, for example, control the passing of coolant into and out of the coolant channels. In some embodiments, the handle automatically passes coolant into and out of the coolant channels after a certain amount of time and/or as the device reaches a certain threshold temperature. In some embodiments, the handle automatically stops passage of coolant into and out of the coolant channels after a certain amount of time and/or as the temperature of the device drops below a certain threshold temperature. In some embodiments, the handle is manually controlled to adjust coolant flow.

Figure 5:
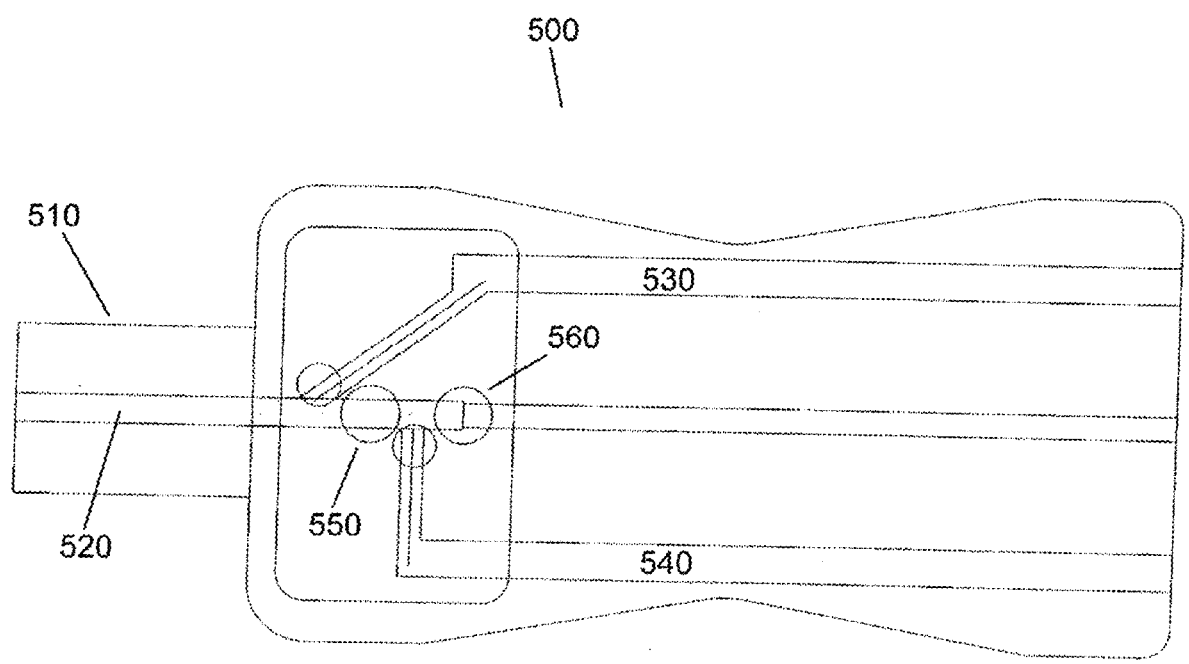
FIG. 5 shows a schematic drawing of a handle configured to control the passing of coolant into and out of the coolant channels.

FIG. 5 shows a schematic drawing of a handle configured to control the passing of coolant into and out of the coolant channels. As shown in FIG. 5, the handle 500 is engaged with a coaxial transmission line 510 having a coolant channel 520. The handle 500 has therein a coolant input channel 530, a coolant output channel 540, a first blocking component 550 (e.g., a screw or pin) configured to prevent flow through channel 520 behind the blocking component and a second blocking component 560. The coolant input channel 530 is configured to provide coolant to the coolant channel 520. The coolant output channel 540 is configured to remove coolant from the coolant channel 520 (e.g., coolant that has circulated and removed heat from a device). The coolant input channel 530 and coolant output channel 540 are not limited to particular sizes or means for providing and removing coolant. The first blocking components 550 and second blocking component 560 are not limited to particular sizes or shapes. In some embodiments, the first blocking component 550 and second blocking component 560 each have a circular shape and a size that matches the diameter of the coolant input channel 530 and the coolant output channel 540. In some embodiments, the first blocking component 550 and second blocking component 560 are used to block the backflow of coolant to a certain region of the handle 500. In some embodiments, the blocking components are configured such that only a portion (e.g., 1%, 5%, 10%, 20%, 50%, 75%, 85%, 95%, 99%) of the channel is blocked. Blocking only a portion permits the user, for example, to vary the pressure gradients within the coolant channel 520.

Energy delivery devices having coolant passage channels allow for adjustment of the characteristic impedance of the coaxial transmission line. In particular, the dielectric properties of the coolant (or of a non-coolant material that is passed through the channel(s)) may be adjusted to alter the bulk complex permittivity of the dielectric medium separating the outer and inner conductors. As such, changes in the characteristic impedance are made during a procedure to, for example, optimize energy delivery, tissue effects, temperature, or other desired properties of the system, device, or application. In other embodiments, a flow material is selected prior to a procedure based on the desired parameters and maintained throughout the entire procedure. Thus, such devices provide an antenna radiating in a changing dielectric environment to be adjusted to resonate in the changing environment to, for example, allow adaptive tuning of the antenna to ensure peak efficiency of operation. As desired, the fluid flow also allows heat transfer to and from the coaxial cable. In some embodiments, the channels or hollowed out areas contain a vacuum or partial vacuum. In some embodiments, impedance is varied by filling the vacuum with a material (e.g., any material that provides the desired result). Adjustments may be made at one or more time points or continuously.

The energy delivery devices having coolant passage channels are not limited to particular aspects of the channels. In some embodiments, the channel is cut through only a portion of the outer or inner conductor and/or solid dielectric material so that the flowed material is in contact with either the inner or outer conductor and the remaining dielectric material. In some embodiments, the channels are linear along the length of the coaxial cable. In some embodiments, the channels are non-linear. In some embodiments, where more than one channel is used, the channels run parallel to one another. In other embodiments, the channels are not parallel. In some embodiments, the channels cross one another. In some embodiments, the channels remove over 50% (e.g., 60%, 70%, 80%, etc.) of the outer or inner conductor and/or solid dielectric material. In some embodiments, the channels remove substantially all of the outer or inner conductor and/or solid dielectric material.

The energy delivery devices having coolant passage channels are not limited by the nature of the material that is flowed through the outer or inner conductor and/or solid dielectric material. In some embodiments, the material is selected to maximize the ability to control the characteristic impedance of the device, to maximize heat transfer to or from the coaxial cable, or to optimize a combination of control of the characteristic impedance and heat transfer. In some embodiments, the material that is flowed through the outer or inner conductor and/or solid dielectric material is a liquid. In some embodiments, the material is a gas. In some embodiments, the material is a combination of liquid or gas. The present invention is not limited to the use of liquids or gasses. In some embodiments, the material is a slurry, a gel, or the like. In some embodiments, a coolant fluid is used. Any coolant fluid now known or later developed may be used. Exemplary coolant fluids include, but are not limited to, one or more of or combinations of, water, glycol, air, inert gasses, carbon dioxide, nitrogen, helium, sulfur hexafluoride, ionic solutions (e.g., sodium chloride with or without potassium and other ions), dextrose in water, Ringer's lactate, organic chemical solutions (e.g., ethylene glycol, diethylene glycol, or propylene glycol), oils (e.g., mineral oils, silicone oils, fluorocarbon oils), liquid metals, freons, halomethanes, liquified propane, other haloalkanes, anhydrous ammonia, sulfur dioxide. In some embodiments, the coolant fluids are pre-cooled prior to delivery into the energy deliver device. In some embodiments, the coolant fluids are cooled with a cooling unit following entry into the energy delivery device. In some embodiments, the material passed through the dielectric material is designed to generate an endothermic reaction upon contact with an additional material.

The energy delivery devices having coolant passage channels are configured to permit control over the parameters of fluid infusion through the device. In some embodiments, the device is manually adjusted by the user (e.g., a treating physician or technician) as desired. In some embodiments, the adjustments are automated. In some embodiments, the devices are configured with or used with sensors that provide information to the user or the automated systems (e.g., comprising processors and/or software configured for receiving the information and adjusting fluid infusion or other device parameters accordingly). Parameters that may be regulated include, but are not limited to, speed of infusion of the fluid, concentration of ions or other components that affect the properties of the fluid (e.g., dielectric properties, heat transfer properties, flow rate, etc.), temperature of the fluid, type of fluid, mixture ratios (e.g., mixtures of gas/fluid for precise tuning or cooling). Thus, energy delivery devices having coolant passage channels are configured to employ a feed-back loop that can change one or more desired parameters to tune the device (e.g., antenna) more accurately, or speed up the infusion of the fluid if the device, portions of the device, or tissue of the subject reaches an undesired temperature (or a temperature for an undesired period of time).

The energy delivery devices having coolant passage channels provide numerous advantages over the currently available systems and devices. For example, by providing a coaxial transmission line with channels carved out of, and that can substantially remove the volume of solid dielectric material, the coaxial transmission line may be designed such that it can fit within very small needles (e.g., 18-20 gauge needles or smaller). Typically, medical devices configured to delivery microwave energy are designed to fit within large needles due to bulky dielectric materials. Other devices use a cooling external water jacket that also increases probe size and can increase tissue damage. These large probe sizes increase the risk of complications when used in the chest and abdomen. In some embodiments of the present invention, the maximum outer diameter of the portion of the device that enters a subject is 16-18 gauge or less (20 gauge or less).

Figure 6:
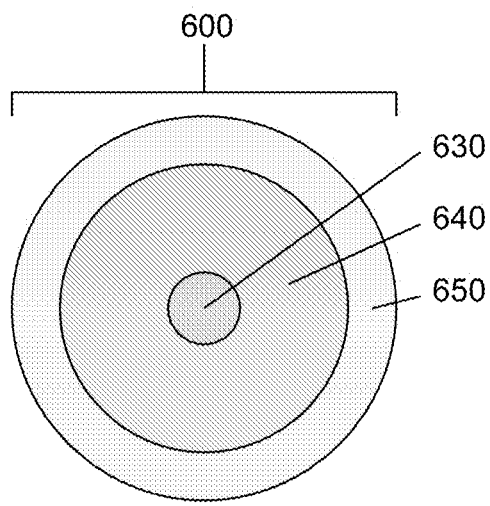
FIG. 6 shows a transverse cross-section schematic of coaxial cable embodiments having coolant passages.
Figure 6:
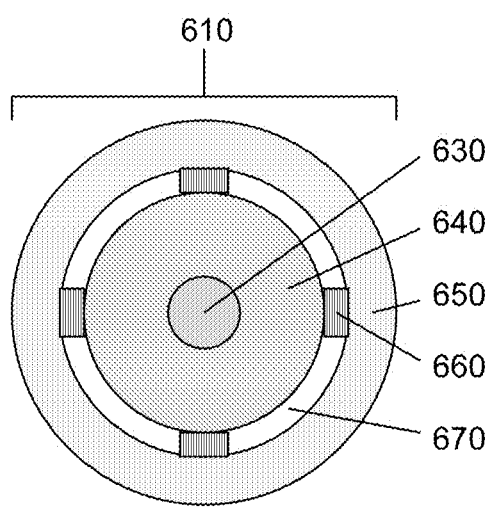
Figure 6:
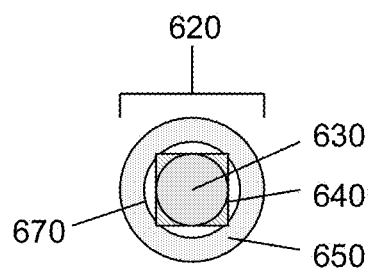

FIG. 6 shows a transverse cross-section schematic of standard coaxial cable embodiments and embodiments of the present invention having coolant passages. As shown in FIG. 6, a conventional coaxial cable 600 and two exemplary coaxial cables of the present invention, 610 and 620 are provided. A coaxial cable is made, generally, of three separate spaces: a metallic inner conductor 630, a metallic outer conductor 650, and a space between them. The space between them is usually filled with a low-loss dielectric material 640 (e.g., polyfluorotetraethylene, or PTFE) to mechanically support the inner conductor and maintain it with the outer conductor. The characteristic impedance of a coaxial cable is fixed by the ratio of diameters of the inner conductor and dielectric material (i.e., inner diameter of the outer conductor) and the permittivity of the space between them. Usually, the permittivity is fixed because of the solid polymer comprising it. However, in embodiments of the present invention, a fluid with variable permittivity (or conductivity) at least partially occupies this space, permitting the characteristic impedance of the cable to be adjusted.

Still referring to FIG. 6, in one embodiment of the present invention, the coaxial cable 610 has the outer portion of the dielectric material removed to create a channel between the dielectric material 640 and the outer conductor 650. In the embodiments shown, the created space is separated into four distinct channels 670 by the addition of support lines 660 configured to maintain the space between the outer conductor 650 and the solid dielectric material 640. The support lines 660 may be made of any desired material and may be the same or a different material as the solid dielectric material 640. In some embodiments, so as to avoid undesired heating of the device (e.g., undesired heating of the outer conductor), the support lines 660 are made of a biocompatible and meltable material (e.g., wax). The presence of multiple channels permits one or more of the channels to permit flow in one direction (towards the proximal end of the cable) and one or more other channels to permit flow in the opposite direction (towards the distal end of the cable).

Still referring to FIG. 6, in another embodiment, the coaxial cable 620 has a substantial portion of the solid dielectric material 640 removed. Such an embodiment may be generated, for example, by stripping away the solid dielectric material 640 down to the surface of inner conductor 630 on each of four sides. In another embodiment, strips of dielectric material 640 are applied to an inner conductor 630 to create the structure. In this embodiment, four channels 670 are created. By removing a substantial amount of the dielectric material 640, the diameter of the outer conductor 650 is substantially reduced. The corners provided by the remaining dielectric material 640 provide the support to maintain the position of the outer conductor 650 with respect to the inner conductor 630. In this embodiment, the overall diameter of the coaxial cable 620 and the device is substantially reduced.

Figure 7:
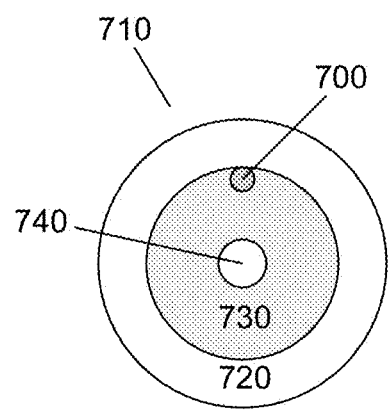
FIG. 7 shows a coolant circulating tube (e.g., coolant needle, catheter) positioned within an energy emission device having an outer conductor and a dielectric material.

In some embodiments, the devices have a coolant passage formed through insertion of a tube configured to circulate coolant through the dielectric portion or inner or outer conductors of any of the energy emission devices of the present invention. FIG. 7 shows a coolant circulating tube 700 (e.g., coolant needle, catheter) positioned within an energy emission device 710 having an outer conductor 720, a dielectric material 730, and an inner conductor 740. As shown in FIG. 7, the tube 700 is positioned along the outside edge of the dielectric material 730 and inside edge of the outer conductor 720, with the inner conductor 740 positioned approximately in the center of the dielectric material 730. In some embodiments, the tube 700 is positioned within the dielectric material 730 such that it does not contact the outer conductor 720. In some embodiments, the tube 700 has multiple channels (not shown) for purposes of recirculating the coolant within the tube 700 without passing the coolant into the dielectric material 730 and/or the outer conductor 720, thereby cooling the dielectric material 730 and/or the outer conductor 720 with the exterior of the tube 700.

Energy Delivery Device with a Center Fed Dipole

In some embodiments, the energy delivery systems of the present invention utilize energy delivery devices employing a center fed dipole component (see, e.g., U.S. patent application Ser. No. 11/728,457; herein incorporated by reference in its entirety). The devices are not limited to particular configurations. In some embodiments, the devices have therein a center fed dipole for heating a tissue region through application of energy (e.g., microwave energy). In some embodiments, such devices have a coaxial cable connected to a hollow tube (e.g., where the interior diameter is at least 50% of the exterior diameter; e.g., where the interior diameter is substantially similar to the exterior diameter). The coaxial cable may be a standard coaxial cable, or it may be a coaxial cable having therein a dielectric component with a near-zero conductivity (e.g., air). The hollow tube is not limited to a particular design configuration. In some embodiments, the hollow tube assumes the shape of (e.g., diameter of), for example, a 20-gauge needle. Preferably, the hollow tube is made of a solid, rigid conductive material (e.g., any number of metals, conductor-coated ceramics or polymers, etc.). In some embodiments, the hollow tube is configured with a sharpened point or the addition of a stylet on its distal end to permit direct insertion of the device into a tissue region without the use of, for example, a cannula. The hollow tube is not limited to a particular composition (e.g., metal, plastic, ceramic). In some embodiments, the hollow tube comprises, for example, copper or copper alloys with other hardening metals, silver or silver alloys with other hardening metals, gold-plated copper, metal-plated Macor (machinable ceramic), metal-plated hardened polymers, and/or combinations thereof.

In some embodiments, the center fed dipole is configured to adjust the energy delivery characteristics in response to heating so as to provide a more optimal energy delivery throughout the time period of a process. In some embodiments, this is achieved by using a material that changes volume in response to temperature changes such that the change in the volume of the material changes to the energy delivery characteristics of the device. In some embodiments, for example, an expandable material is placed in the device such that the resonant portion of the center fed dipole component or the stylet is pushed distally along the device in response to heating. This changes the tuning of the device to maintain a more optimal energy delivery. The maximum amount of movement can be constrained, if desired, by, for example, providing a locking mechanism that prevents extension beyond a particular point.

The energy delivery devices employing a center fed dipole component are not limited by the manner in which the hollow tube is connected to the coaxial cable. In some embodiments, a portion of the outer conductor at the distal end of the coaxial cable feedline is removed, exposing a region of solid dielectric material. The hollow tube can be positioned onto the exposed dielectric material and attached by any means. In some some embodiments, a physical gap between the outer conductor and the hollow tube is provided. In some some embodiments, the hollow tube is capacitively or conductively attached to the feedline at its center point such that the electrical length of the hollow tube comprises a frequency-resonant structure when inserted into tissue.

In use, the energy delivery devices employing a center fed dipole component are configured such that an electric field maximum is generated at the open distal end of the hollow tube. In some embodiments, the distal end of the hollow tube has a pointed shape so as to assist in inserting the device though a subject and into a tissue region. In some embodiments, the entire device is hard and rigid so as to facilitate linear and direct insertion directly to a target site. In some embodiments, the structure resonates at, for example, ~2.45 GHz, as characterized by a minimum in the reflection coefficient (measured at the proximal end of the feedline) at this frequency. By changing the dimensions of the device (e.g., length, feed point, diameter, gap, etc.) and materials (dielectric materials, conductors, etc.) of the antenna, the resonant frequency may be changed. A low reflection coefficient at a desired frequency ensures efficient transmission of energy from the antenna to the medium surrounding it.

Preferably, the hollow tube is of length $\lambda/2$, where $\lambda$ is the electromagnetic field wavelength in the medium of interest (e.g., ~18 cm for 2.45 GHz in liver) to resonate within the medium. In some embodiments, the length of the hollow tube is approximately $\lambda/2$, where $\lambda$ is the electromagnetic field wavelength in the medium of interest to resonate within the medium, such that a minimum of power reflection at the proximal end is measured. However, deviations from this length may be employed to generate resonant wavelengths (e.g., as the surrounding materials are changed). Preferably, the inner conductor of a coaxial cable is extended with its distal end at the tube center (e.g., at λ/4 from the end of the tube) and configured such that the inner conductor maintains electrical contact at the tube center, although deviations from this position are permitted (e.g., to generate resonant wavelengths).

The hollow tube portion of the present invention may have a wide variety of shapes. In some embodiments, the tube is cylindrical throughout its length. In some embodiments, tube tapers from a center position such that it has a smaller diameter at its end as compared to its center. Having a smaller point at the distal end assists in penetrating a subject to arrive at the target region. In some embodiments, where the shape of the hollow tube deviates from a cylindrical shape, the tube maintains a symmetrical structure on either side of its longitudinal center. However, the devices are not limited by the shape of the hollow tube, so long as the functional properties are achieved (i.e., the ability to deliver desired energy to a target region).

In some embodiments, the center-fed dipole components may be added to the distal end of a wide variety of ablation devices to provide the benefits described herein. Likewise, a wide variety of devices may be modified to accept the center-fed dipole components of the present invention.

In some embodiments, the devices have a small outer diameter. In some embodiments, the center-fed dipole component of the invention is directly used to insert the invasive component of the device into a subject. In some such embodiments, the device does not contain a cannula, allowing for the invasive components to have a smaller outer diameter. For example, the invasive component can be designed such that it fits within or is the size of very small needles (e.g., 18-20 gauge needles or smaller).

Figure 8:
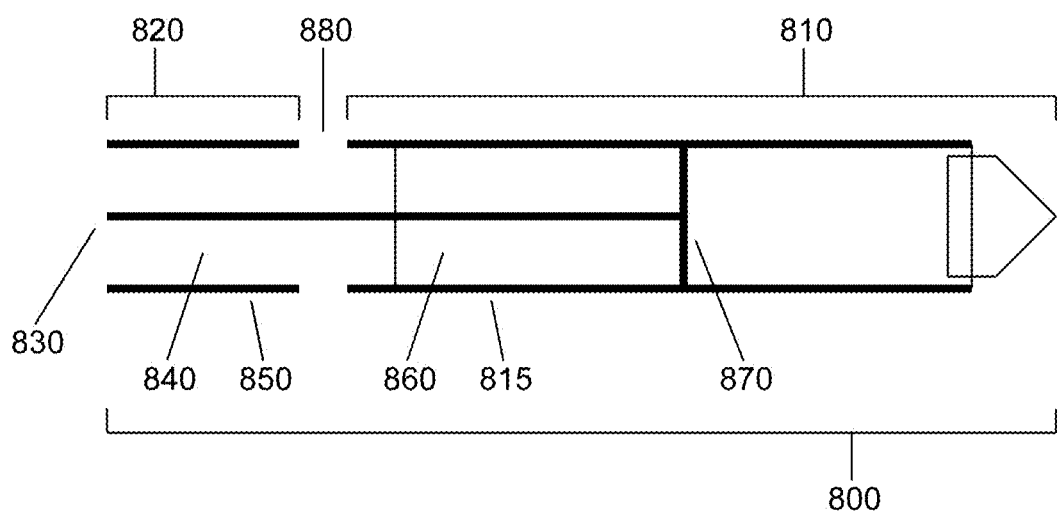
FIG. 8 schematically shows the distal end of a device (e.g., antenna of an ablation device) of the present invention that comprises a center fed dipole component of the present invention.

FIG. 8 schematically shows the distal end of a device 800 (e.g., antenna of an ablation device) of the present invention that comprises a center fed dipole component 810 of the present invention. One skilled in the art will appreciate any number of alternative configurations that accomplish the physical and/or functional aspects of the present invention. As shown, the center fed dipole device 800 has therein a hollow tube 815, a coaxial transmission line 820 (e.g., a coaxial cable), and a stylet 890. The center fed dipole device 800 is not limited to a particular size. In some embodiments, the size of the center fed dipole device 800 is small enough to be positioned at a tissue region (e.g., a liver) for purposes of delivering energy (e.g., microwave energy) to that tissue region.

Referring again to FIG. 8, the hollow tube 815 is not limited to a particular material (e.g., plastic, ceramic, metal, etc.). The hollow tube 815 is not limited to a particular length. In some embodiments, the length of the hollow tube is λ/2, where λ is the electromagnetic field wavelength in the medium of interest (e.g., ~18 cm for 2.45 GHz in liver). The hollow tube 815 engages the coaxial transmission line 820 such that the hollow tube 815 is attached to the coaxial transmission line 820 (described in more detail below). The hollow tube 815 has therein a hollow tube matter 860. The hollow tube 815 is not limited to a particular type of hollow tube matter. In some embodiments, the hollow tube matter 860 is air, fluid or a gas.

Still referring to FIG. 8, the hollow tube 815 is not limited to a particular shape (e.g., cylindrical, triangular, squared, rectangular, etc.). In some embodiments, the shape of the hollow tube 815 is of a needle (e.g., a 20-gauge needle, an 18-gauge needle). In some embodiments, the hollow tube 815 is divided into two portions each of variable length. As shown, the hollow tube 815 is divided into two portions each of equal length (e.g., each portion having a length of λ/4). In such embodiments, the shapes of each portion are symmetrical. In some embodiments, the hollow tube has a diameter equal to or less than a 20-gauge needle, a 17-gauge needle, a 12-gauge needle, etc.

Still referring to FIG. 8, the distal end of the hollow tube 815 engages a stylet 890. The device 800 is not limited to a particular stylet 890. In some embodiments, the stylet 890 is designed to facilitate percutaneous insertion of the device 800. In some embodiments, the stylet 890 engages the hollow tube 815 by sliding inside the hollow tube 815 such that the stylet 890 is secured.

Still referring to FIG. 8, the coaxial transmission line 820 is not limited to a particular type of material. In some embodiments, the proximal coaxial transmission line 820 is constructed from commercial-standard 0.047-inch semi-rigid coaxial cable. In some embodiments, the coaxial transmission line 820 is metal-plated (e.g., silver-plated, copper-plated), although the present invention is not so limited. The proximal coaxial transmission line 820 is not limited to a particular length.

Still referring to FIG. 8, in some embodiments, the coaxial transmission line 820 has a coaxial center conductor 830, a coaxial dielectric material 840, and a coaxial outer conductor 850. In some embodiments, the coaxial center conductor 830 is configured to conduct cooling fluid along its length. In some embodiments, the coaxial center conductor 830 is hollow. In some embodiments, the coaxial center conductor 830 has a diameter of, for example, 0.012 inches. In some embodiments, the coaxial dielectric material 840 is polyfluorotetraethylene (PTFE). In some embodiments, the coaxial dielectric material 840 has a near-zero conductivity (e.g., air, fluid, gas).

Still referring to FIG. 8, the distal end of the coaxial transmission line 820 is configured to engage the proximal end of the hollow tube 815. In some embodiments, the coaxial center conductor 830 and the coaxial dielectric material 840 extend into the center of the hollow tube 815. In some embodiments, the coaxial center conductor 820 extends further into the hollow tube 815 than the coaxial dielectric material 840. The coaxial center conductor 820 is not limited to a particular amount of extension into the hollow tube 815. In some embodiments, the coaxial center conductor 820 extends a length of λ/4 into the hollow tube 815. The distal end of the coaxial transmission line 820 is not limited to a particular manner of engaging the proximal end of the hollow tube 815. In some embodiments, the proximal end of the hollow tube engages the coaxial dielectric material 840 so as to secure the hollow tube 815 with the coaxial transmission line 820. In some embodiments, where the coaxial dielectric material 840 has a near-zero conductivity, the hollow tube 815 is not secured with the coaxial transmission line 820. In some embodiments, the distal end of the coaxial center conductor 830 engages the walls of the hollow tube 815 directly or though contact with a conductive material 870, which may be made of the same material as the coaxial center conductor or may be of a different material (e.g., a different conductive material).

Still referring to FIG. 8, in some embodiments, a gap 880 exists between the distal end of the coaxial transmission line outer conductor 850 and the hollow tube 815 thereby exposing the coaxial dielectric material 840. The gap 880 is not limited to a particular size or length. In some embodiments, the gap 880 ensures an electric field maximum at the proximal end of the coaxial transmission line 880 and the distal open end of the hollow tube 815. In some embodiments, the center fed dipole device 810 resonates at ~2.45

GHz, as characterized by a minimum in the reflection coefficient at this frequency. By changing the dimensions (length, feed point, diameter, gap, etc.) and materials (dielectric materials, conductors, etc.) of the device the resonant frequency may be changed. A low reflection coefficient at this frequency ensures efficient transmission of energy from the antenna to the medium surrounding it.

Still referring to FIG. 8, in some embodiments, the gap 880 is filled with a material (e.g., epoxy) so bridge the coaxial transmission line 820 and the hollow tube 815. The devices are not limited to a particular type or kind of substantive material. In some embodiments, the substantive material does not interfere with the generation or emission of an energy field through the device. In some embodiments, the material is biocompatible and heat resistant. In some embodiments, the material lacks or substantially lacks conductivity. In some embodiments, the material further bridges the coaxial transmission line 820 and the hollow tube 815 with the coaxial center conductor 830. In some embodiments, the substantive material is a curable resin. In some embodiments, the material is a dental enamel (e.g., XRV Herculite enamel; see, also, U.S. Pat. Nos. 6,924,325, 6,890,968, 6,837,712, 6,709,271, 6,593,395, and 6,395,803, each herein incorporated by reference in their entireties). In some embodiments, the substantive material is cured (e.g., cured with a curing light such as, for example, L.E. Demetron II curing light) (see, e.g., U.S. Pat. Nos. 6,994,546, 6,702,576, 6,602,074 and 6,435,872). Thus, the present invention provides ablation devices comprising a cured enamel resin. Such a resin is biocompatible and rigid and strong.

Energy Delivery Devices Having a Linear Array of Antenna Components

In some embodiments, the energy delivery systems of the present invention utilize energy delivery devices having a linear array of antennae components (see, e.g., U.S. Provisional Patent Application No. 60/831,055; herein incorporated by reference in its entirety). The devices are not limited to particular configurations. In some embodiments, the energy delivery devices having a linear array of antennae components have therein an antenna comprising an inner conductor and an outer conductor, wherein the outer conductor is provided in two or more linear segments separated by gaps, such that the length and position of the segments is configured for optimized delivery of energy at the distal end of the antenna. For example, in some embodiments, an antenna comprises a first segment of outer conductor that spans the proximal end of the antenna to a region near the distal end and a second segment of outer conductor distal to the first segment wherein a gap separates or partially separates the first and second segments. The gaps may entirely circumscribe the outer conductor or may only partially circumscribe the outer conductor. In some embodiments, the length of the second segment is $\lambda/2$, $\lambda/4$, etc., although the present invention is not so limited. In some embodiments one or more additional (e.g., third, fourth, fifth) segments are provided distal to the second segment, each of which is separated from the other by a gap. In some embodiments, the antenna is terminated with a conductive terminal end that is in electronic communication with the inner conductor. In some embodiments, the conductive terminal end comprises a disc having a diameter substantially identical to the diameter of the outer conductor. Such antennae provide multiple peaks of energy delivery along the length of the distal end of the antenna, providing a broader region of energy delivery to target larger regions of tissue. The location and position of the peaks is controlled by selecting the length of the outer conductor segments and by controlling the amount of energy delivered.

The energy delivery devices having a linear array of antennae components are not limited by the nature of the various components of the antenna. A wide variety of components may be used to provide optimal performance, including, but not limited to, the use of a variety of materials for the inner and outer conductors, the use of a variety of materials and configurations for dielectric material between the inner and outer conductors, the use of coolants provided by a variety of different methods.

In certain embodiments, the devices comprise a linear antenna, wherein the linear antenna comprises an outer conductor enveloped around an inner conductor, wherein the inner conductor is designed to receive and transmit energy (e.g., microwave energy), wherein the outer conductor has therein a series of gap regions (e.g., at least two) positioned along the outer conductor, wherein the inner conductor is exposed at the gap regions, wherein the energy transmitting along the inner conductor is emitted through the gap regions. The devices are not limited to a particular number of gap regions (e.g., 2, 3, 4, 5, 6, 10, 20, 50). In some embodiments, the positioning of the gaps is configured for, for example, linear ablation. In some embodiments, the inner conductor comprises a dielectric layer enveloping a central transmission line. In some embodiments, the dielectric element has near-zero conductivity. In some embodiments, the device further comprises a stylet. In some embodiments, the device further comprises a tuning element for adjusting the amount of energy delivered through the gap regions. In certain embodiments, when used in tissue ablation settings, the device is configured to deliver a sufficient amount of energy to ablate a tissue region or cause thrombosis.

The energy delivery devices having a linear array of antennae components provide numerous advantages over the currently available systems and devices. For example, a major drawback with currently available medical devices that utilize microwave energy is that the emitted energy is provided locally, thereby precluding delivery of energy over a deeper and denser scale. The devices of the present invention overcome this limitation by providing an applicator device having a linear array of antennae components configured to deliver energy (e.g., microwave energy) over a wider and deeper scale (e.g., as opposed to local delivery). Such a device is particularly useful in the tissue ablation of dense and/or thick tissue regions (e.g., tumors, organ lumens) and particularly deep tissue regions (e.g., large cardiac areas, brains, bones).

III. Processor

In some embodiments, the energy delivery systems of the present invention utilize processors that monitor and/or control one or more of the components of the system. In some embodiments, the processor is provided within a computer module. The computer module may also comprise software that is used by the processor to carry out one or more of its functions. For example, in some embodiments, the systems of the present invention provide software for regulating the amount of microwave energy provided to a tissue region through monitoring one or more characteristics of the tissue region including, but not limited to, the size and shape of a target tissue, the temperature of the tissue region, and the like (e.g., through a feedback system) (see, e.g., U.S. patent application Ser. Nos. 11/728,460, 11/728,457, and 11/728,428; each of which is herein incorporated by reference in their entireties). In some embodiments, the software is configured to provide information (e.g., monitoring information) in real time. In some embodiments, the software is configured to interact with the energy delivery systems of the present invention such that it is able to raise or lower (e.g., tune) the amount of energy delivered to a tissue region. In some embodiments, the software is designed to prime coolants for distribution into, for example, an energy delivery device such that the coolant is at a desired temperature prior to use of the energy delivery device. In some embodiments, the type of tissue being treated (e.g., liver) is inputted into the software for purposes of allowing the processor to regulate (e.g., tune) the delivery of microwave energy to the tissue region based upon pre-calibrated methods for that particular type of tissue region. In other embodiments, the processor generates a chart or diagram based upon a particular type of tissue region displaying characteristics useful to a user of the system. In some embodiments, the processor provides energy delivering algorithms for purposes of, for example, slowly ramping power to avoid tissue cracking due to rapid out-gassing created by high temperatures. In some embodiments, the processor allows a user to choose power, duration of treatment, different treatment algorithms for different tissue types, simultaneous application of power to the antennas in multiple antenna mode, switched power delivery between antennas, coherent and incoherent phasing, etc. In some embodiments, the processor is configured for the creation of a database of information (e.g., required energy levels, duration of treatment for a tissue region based on particular patient characteristics) pertaining to ablation treatments for a particular tissue region based upon previous treatments with similar or dissimilar patient characteristics.

In some embodiments, the processor is used to generate, for example, an ablation chart based upon entry of tissue characteristics (e.g., tumor type, tumor size, tumor location, surrounding vascular information, blood flow information, etc.). In such embodiments, the processor could direct placement of the energy delivery device so as to achieve desired ablation based upon the ablation chart.

In some embodiments a software package is provided to interact with the processor that allows the user to input parameters of the tissue to be treated (e.g., type of tumor or tissue section to be ablated, size, where it is located, location of vessels or vulnerable structures, and blood flow information) and then draw the desired ablation zone on a CT or other image to provide the desired results. The probes may be placed into the tissue, and the computer generates the expected ablation zone based on the information provided. Such an application may incorporate feedback. For example, CT, MRI, or ultrasound imaging or thermometry may be used during the ablation. This data is fed back into the computer, and the parameters readjusted to produce the desired result.

As used herein, the terms "computer memory" and "computer memory device" refer to any storage media readable by a computer processor. Examples of computer memory include, but are not limited to, random access memory (RAM), read-only memory (ROM), computer chips, optical discs (e.g., compact discs (CDs), digital video discs (DVDs), etc.), magnetic disks (e.g., hard disk drives (HDDs), floppy disks, ZIP® disks, etc.), magnetic tape, and solid state storage devices (e.g., memory cards, "flash" media, etc.).

As used herein, the term "computer readable medium" refers to any device or system for storing and providing information (e.g., data and instructions) to a computer processor. Examples of computer readable media include, but are not limited to, optical discs, magnetic disks, magnetic tape, solid-state media, and servers for streaming media over networks.

As used herein, the terms "processor" and "central processing unit" or "CPU" are used interchangeably and refer to a device that is able to read a program from a computer memory device (e.g., ROM or other computer memory) and perform a set of steps according to the program.

IV. Imaging Systems

In some embodiments, the energy delivery systems of the present invention utilize imaging systems comprising imaging devices. The energy delivery systems are not limited to particular types of imaging devices (e.g., endoscopic devices, stereotactic computer assisted neurosurgical navigation devices, thermal sensor positioning systems, motion rate sensors, steering wire systems, intraprocedural ultrasound, fluoroscopy, computerized tomography magnetic resonance imaging, nuclear medicine imaging devices triangulation imaging, thermoacoustic imaging, infrared and/or laser imaging, electromagnetic imaging) (see, e.g., U.S. Pat. Nos. 6,817,976, 6,577,903, and 5,697,949, 5,603,697, and International Patent Application No. WO 06/005,579; each herein incorporated by reference in their entireties). In some embodiments, the systems utilize endoscopic cameras, imaging components, and/or navigation systems that permit or assist in placement, positioning, and/or monitoring of any of the items used with the energy systems of the present invention.

In some embodiments, the energy delivery systems provide software that is configured for use of imaging equipment (e.g., CT, MRI, ultrasound). In some embodiments, the imaging equipment software allows a user to make predictions based upon known thermodynamic and electrical properties of tissue, vasculature, and location of the antenna(s). In some embodiments, the imaging software allows the generation of a three-dimensional map of the location of a tissue region (e.g., tumor, arrhythmia), location of the antenna(s), and to generate a predicted map of the ablation zone.

In some embodiments, the imaging systems of the present invention are used to monitor ablation procedures (e.g., microwave thermal ablation procedures, radio-frequency thermal ablation procedures). The present invention is not limited to a particular type of monitoring. In some embodiments, the imaging systems are used to monitor the amount of ablation occurring within a particular tissue region(s) undergoing a thermal ablation procedure. In some embodiments, the monitoring operates along with the ablation devices (e.g., energy delivery devices) such that the amount of energy delivered to a particular tissue region is dependent upon the imaging of the tissue region. The imaging systems are not limited to a particular type of monitoring. The present invention is not limited to what is being monitored with the imaging devices. In some embodiments, the monitoring is imaging blood perfusion for a particular region so as to detect changes in the region, for example, before, during and after a thermal ablation procedure. In some embodiments, the monitoring includes, but is not limited to, MRI imaging, CT imaging, ultrasound imaging, nuclear medicine imaging, and fluoroscopy imaging. For example, in some embodiments, prior to a thermal ablation procedure, a contrast agent (e.g., iodine or other suitable CT contrast agent; gadolinium chelate or other suitable MRI contrast agent, microbubbles or other suitable ultrasound contrast agent, etc.) is supplied to a subject (e.g., a patient) and the contrast agent perfusing through a particular tissue region that is undergoing the ablation procedure is monitored for blood perfusion changes.

In some embodiments, the imaging systems are designed to automatically monitor a particular tissue region at any desired frequency (e.g., per second intervals, per one-minute intervals, per ten-minute intervals, per hour-intervals, etc.). In some embodiments, the present invention provides software designed to automatically obtain images of a tissue region (e.g., MRI imaging, CT imaging, ultrasound imaging, nuclear medicine imaging, fluoroscopy imaging), automatically detect any changes in the tissue region (e.g., blood perfusion, temperature, amount of necrotic tissue, etc.), and based on the detection to automatically adjust the amount of energy delivered to the tissue region through the energy delivery devices. Likewise, an algorithm may be applied to predict the shape and size of the tissue region to be ablated (e.g., tumor shape) such that the system recommends the type, number, and location of ablation probes to effectively treat the region. In some embodiments, the system is configured to with a navigation or guidance system (e.g., employing triangulation or other positioning routines) to assist in or direct the placement of the probes and their use.

For example, such procedures may use the enhancement or lack of enhancement of a contrast material bolus to track the progress of an ablation or other treatment procedure. Subtraction methods may also be used (e.g., similar to those used for digital subtraction angiography). For example, a first image may be taken at a first time point. Subsequent images subtract out some or all of the information from the first image so that changes in tissue are more readily observed. Likewise, accelerated imaging techniques may be used that apply "under sampling" techniques (in contrast to Nyquist sampling). It is contemplated that such techniques provide excellent signal-to-noise using multiple low resolutions images obtained over time. For example, an algorithm called HYPER (highly constrained projection reconstruction) is available for MRI that may be applied to embodiments of the systems of the invention.

As thermal-based treatments coagulate blood vessels when tissue temperatures exceed, for example, 50° C., the coagulation decreases blood supply to the area that has been completely coagulated. Tissue regions that are coagulated do not enhance after the administration of contrast. In some embodiments, the present invention utilizes the imaging systems to automatically track the progress of an ablation procedure by giving, for example, a small test injection of contrast to determine the contrast arrival time at the tissue region in question and to establish baseline enhancement. In some embodiments, a series of small contrast injections is next performed following commencement of the ablation procedure (e.g., in the case of CT, a series of up to fifteen 10 ml boluses of 300 mgI/ml water soluble contrast is injected), scans are performed at a desired appropriate post-injection time (e.g., as determined from the test injection), and the contrast enhancement of the targeted area is determined using, for example, a region-of-interest (ROI) to track any one of a number of parameters including, but not limited to, attenuation (Hounsfield Units [HU]) for CT, signal (MRI), echogenicity (ultrasound), etc. The imaged data is not limited to a particular manner of presentation. In some embodiments, the imaging data is presented as color-coded or grey scale maps or overlays of the change in attenuation/signal/echogenicity, the difference between targeted and non-targeted tissue, differences in arrival time of the contrast bolus during treatment, changes in tissue perfusion, and any other tissue properties that can be measured before and after the injection of contrast material. The methods of the present invention are not limited to selected ROI's, but can be generalized to all pixels within any image. The pixels can be color-coded, or an overlay used to demonstrate where tissue changes have occurred and are occurring. The pixels can change colors (or other properties) as the tissue property changes, thus giving a near real-time display of the progress of the treatment. This method can also be generalized to 3d/4d methods of image display.

In some embodiments, the area to be treated is presented on a computer overlay, and a second overlay in a different color or shading yields a near real-time display of the progress of the treatment. In some embodiments, the presentation and imaging is automated so that there is a feedback loop to a treatment technology (RF, MW, HIFU, laser, cryo, etc) to modulate the power (or any other control parameter) based on the imaging findings. For example, if the perfusion to a targeted area is decreased to a target level, the power could be decreased or stopped. For example, such embodiments are applicable to a multiple applicator system as the power/time/frequency/duty cycle, etc. is modulated for each individual applicator or element in a phased array system to create a precisely sculpted zone of tissue treatment. Conversely, in some embodiments, the methods are used to select an area that is not to be treated (e.g., vulnerable structures that need to be avoided such as bile ducts, bowel, etc.). In such embodiments, the methods monitor tissue changes in the area to be avoided, and warn the user (e.g., treating physician) using alarms (e.g., visible and/or audible alarms) that the structure to be preserved is in danger of damage. In some embodiments, the feedback loop is used to modify power or any other parameter to avoid continued damage to a tissue region selected not to be treated. In some embodiments, protection of a tissue region from ablation is accomplished by setting a threshold value such as a target ROI in a vulnerable area, or using a computer overlay to define a "no treatment" zone as desired by the user.

V. Tuning Systems

In some embodiments, the energy delivery systems of the present invention utilize tuning elements for adjusting the amount of energy delivered to the tissue region. In some embodiments, the tuning element is manually adjusted by a user of the system. In some embodiments, a tuning system is incorporated into an energy delivery device so as to permit a user to adjust the energy delivery of the device as desired (see, e.g., U.S. Pat. Nos. 5,957,969, 5,405,346; each herein incorporated by reference in their entireties). In some embodiments, the device is pretuned to the desired tissue and is fixed throughout the procedure. In some embodiments, the tuning system is designed to match impedance between a generator and an energy delivery device (see, e.g., U.S. Pat. No. 5,364,392; herein incorporated by reference in its entirety). In some embodiments, the tuning element is automatically adjusted and controlled by a processor of the present invention (see, e.g., U.S. Pat. No. 5,693,082; herein incorporated by reference in its entirety). In some embodiments, a processor adjusts the energy delivery over time to provide constant energy throughout a procedure, taking into account any number of desired factors including, but not limited to, heat, nature and/or location of target tissue, size of lesion desired, length of treatment time, proximity to sensitive organ areas or blood vessels, and the like. In some embodiments, the system comprises a sensor that provides feedback to the user or to a processor that monitors the function of the device continuously or at time points. The sensor may record and/or report back any number of properties, including, but not limited to, heat at one or more positions of a components of the system, heat at the tissue, property of the tissue, and the like. The sensor may be in the form of an imaging device such as CT, ultrasound, magnetic resonance imaging, or any other imaging device. In some embodiments, particularly for research application, the system records and stores the information for use in future optimization of the system generally and/or for optimization of energy delivery under particular conditions (e.g., patient type, tissue type, size and shape of target region, location of target region, etc.).

VI. Temperature Adjustment Systems

In some embodiments, the energy delivery systems of the present invention utilize coolant systems so as to reduce undesired heating within and along an energy delivery device (e.g., tissue ablation catheter). The systems of the present invention are not limited to a particular cooling system mechanism. In some embodiments, the systems are designed to circulate a coolant (e.g., air, liquid, etc.) throughout an energy delivery device such that the coaxial transmission line(s) and antenna(e) temperatures are reduced. In some embodiments, the systems utilize energy delivery devices having therein channels designed to accommodate coolant circulation. In some embodiments, the systems provide a coolant sheath wrapped around the antenna or portions of the antenna for purposes of cooling the antenna externally (see, e.g., U.S. patent application Ser. No. 11/053,987; herein incorporated by reference in its entirety). In some embodiments, the systems utilize energy delivery devices having a conductive covering around the antenna for purposes of limiting dissipation of heat onto surrounding tissue (see, e.g., U.S. Pat. No. 5,358,515; herein incorporated by reference in its entirety). In some embodiments, upon circulation of the coolant, it is exported into, for example, a waste receptacle. In some embodiments, upon circulation of the coolant it is recirculated.

In some embodiments, the systems utilize expandable balloons in conjunction with energy delivery devices for purposes of urging tissue away from the surface of the antenna(e) (see, e.g., U.S. patent application Ser. No. 11/053,987; herein incorporated by reference in its entirety).

In some embodiments, the systems utilize devices configured to attach onto an energy delivery device for purposes of reducing undesired heating within and along the energy delivery device (see, e.g., U.S. patent application Ser. No. 11/237,430; herein incorporated by reference in its entirety).

VII. Identification Systems

In some embodiments, the energy delivery systems of the present invention utilize identification elements (e.g., RFID elements, barcodes, etc.) associated with one or more components of the system. In some embodiments, the identification element conveys information about a particular component of the system. The present invention is not limited by the information conveyed. In some embodiments, the information conveyed includes, but is not limited to, the type of component (e.g., manufacturer, size, energy rating, tissue configuration, etc.), whether the component has been used before (e.g., so as to ensure that non-sterile components are not used), the location of the component, patient-specific information and the like. In some embodiments, the information is read by a processor of the present invention. In some such embodiments, the processor configures other components of the system for use with, or for optimal use with, the component containing the identification element.

In some embodiments, the energy delivery devices have thereon markings (e.g., scratches, color schemes, etchings, painted contrast agent markings, and/or ridges) so as to improve identification of a particular energy delivery device (e.g., improve identification of a particular device located in the vicinity of other devices with similar appearances). The markings find particular use where multiple devices are inserted into a patient. In such cases, particularly where the devices may cross each other at various angles, it is difficult for the treating physician to associate which proximal end of the device, located outside of the patient body, corresponds to which distal end of the device, located inside the patient body. In some embodiments, a marking (e.g., a number) a present on the proximal end of the device so that it is viewable by the physician's eyes and a second marking (e.g., that corresponds to the number) is present on the distal end of the device so that it is viewable by an imaging device when present in the body. In some embodiments, where a set of antennas is employed, the individual members of the set are numbered (e.g., 1, 2, 3, 4, etc.) on both the proximal and distal ends. In some embodiments, handles are numbered, a matching numbered detachable (e.g., disposable) antennas are connected to the handles prior to use. In some embodiments, a processor of the system ensures that the handles and antennas are properly matched (e.g., by RFID tag or other means). In some embodiments, where the antenna are disposable, the system provides a warning if a disposable component is attempted to be re-used, when it should have been discarded. In some embodiments, the markings improve identification in any type of detection system including, but not limited to, MRI, CT, and ultrasound detection.

The energy delivery systems of the present invention are not limited to particular types of tracking devices. In some embodiments, GPS and GPS related devices are used. In some embodiments, RFID and RFID related devices are used. In some embodiments, barcodes are used.

In such embodiments, authorization (e.g., entry of a code, scanning of a barcode) prior to use of a device with an identification element is required prior to the use of such a device. In some embodiments, the information element identifies that a components has been used before and sends information to the processor to lock (e.g. block) use of system until a new, sterile component is provided.

VIII. Temperature Monitoring Systems

In some embodiments, the energy delivering systems of the present invention utilize temperature monitoring systems. In some embodiments, temperature monitoring systems are used to monitor the temperature of an energy delivery device (e.g., with a temperature sensor). In some embodiments, temperature monitoring systems are used to monitor the temperature of a tissue region (e.g., tissue being treated, surrounding tissue). In some embodiments, the temperature monitoring systems are designed to communicate with a processor for purposes of providing temperature information to a user or to the processor to allow the processor to adjust the system appropriately.

IX. Other Components

The system of the present invention may further employ one or more additional components that either directly or indirectly take advantage of or assist the features of the present invention. For example, in some embodiments, one or more monitoring devices are used to monitor and/or report the function of any one or more components of the system. Additionally, any medical device or system that might be used, directly or indirectly, in conjunction with the devices of the present invention may be included with the system. Such components include, but are not limited to, sterilization systems, devices, and components; other surgical, diagnostic, or monitoring devices or systems; computer equipment; handbooks, instructions, labels, and guidelines; robotic equipment; and the like.

In some embodiments, the systems employ pumps, reservoirs, tubing, wiring, or other components that provide materials on connectivity of the various components of the systems of the present invention. For example, any type of pump may be used to supply gas or liquid coolants to the antennas of the present invention. Gas or liquid handling tanks containing coolant may be employed in the system.

Figure 13:
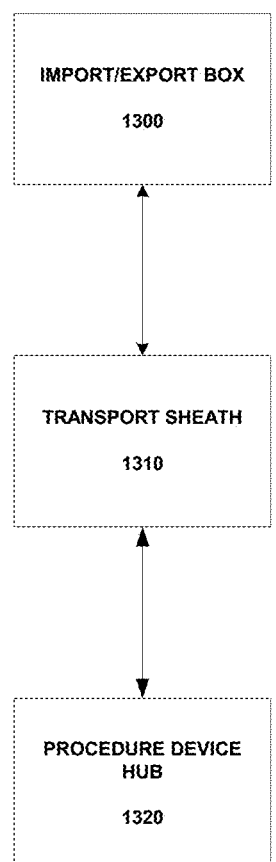
FIG. 13 shows a schematic view of an import/export box, a transport sheath, and a procedure device hub.

In certain embodiments, the energy delivery systems (e.g., the energy delivery device, the processor, the power supply, the imaging system, the temperature adjustment system, the temperature monitoring system, and/or the identification systems) and all related energy delivery system utilization sources (e.g., cables, wires, cords, tubes, pipes providing energy, gas, coolant, liquid, pressure, and communication items) are provided in a manner that reduces undesired presentation problems (e.g., tangling, cluttering, and sterility compromise associated with unorganized energy delivery system utilization sources). The present invention is not limited to a particular manner of providing the energy delivery systems and energy delivery system utilization sources such that undesired presentation problems are reduced. In some embodiments, as shown in FIG. 13, the energy delivery systems and energy delivery system utilization sources are organized with an import/export box 1300, a transport sheath 1310, and a procedure device hub 1320.

The present invention is not limited to a particular type or kind of import/export box. In some embodiments, the import/export box contains the power supply and coolant supply. In some embodiments, the import/export box is located outside of a sterile field in which the patient is being treated. In some embodiments, the import/export box is located outside of the room in which the patient is being treated. In some embodiments, one or more cables connect the import/export box to a procedure device hub. In some embodiments, a single cable is used (e.g., a transport sheath). For example, in some such embodiments, a transport sheath contains components for delivery of both energy and coolant to and/or from the import/export box. In some embodiments, the transport sheath connects to the procedure device hub without causing a physical obstacle for medical practitioners (e.g., travels under the floor, overhead, etc.

The present invention is not limited to a particular type or kind of procedure device hub. In some embodiments, the procedure device hub is configured to receive power, coolant, or other elements from the import/export box or other sources. In some embodiments, the procedure device hub provides a control center, located physically near the patient, for any one or more of: delivering energy to a medical device, circulating coolant to a medical device, collecting and processing data (e.g., imaging data, energy delivery data, safety monitoring data, temperature data, and the like), and providing any other function that facilitates a medical procedure. In some embodiments, the procedure device hub is configured to engage the transport sheath so as to receive the associated energy delivery system utilization sources. In some embodiments, the procedure device hub is configured to receive and distribute the various energy delivery system utilization sources to the applicable devices (e.g., energy delivery devices, imaging systems, temperature adjustment systems, temperature monitoring systems, and/or identification systems). For example, in some embodiments, the procedure device hub is configured to receive microwave energy and coolant from energy delivery system utilization sources and distribute the microwave energy and coolant to an energy delivery device. In some embodiments, the procedure device hub is configured to turn on or off, calibrate, and adjust (e.g., automatically or manually) the amount of a particular energy delivery system utilization source as desired. In some embodiments, the procedure device hub has therein a power splitter for adjusting (e.g., manually or automatically turning on, turning off, calibrating) the amount of a particular energy delivery system utilization source as desired. In some embodiments, the procedure device hub has therein software designed to provide energy delivery system utilization sources in a desired manner. In some embodiments, the procedure device hub has a display region indicating associated characteristics for each energy delivery system utilization source. In some embodiments, the processor associated with the energy delivery system is located in the procedure device hub. In some embodiments, the power supply associated with the energy delivery systems is located within the procedure device hub. In some embodiments, the procedure device hub has a sensor configured to automatically inhibit one or more energy delivery system utilization sources upon the occurrence of an undesired event (e.g., undesired heating, undesired leak, undesired change in pressure, etc.).

In some embodiments, the procedure device hub is designed for location within a sterile setting. In some embodiments, the procedure device hub is positioned on a patient's bed, a table that the patient is on (e.g., a table used for CT imaging, MRI imaging, etc.), or other structure near the patient. In some embodiments, the procedure device hub is positioned on a separate table. In some embodiments, the procedure device hub is attached to a ceiling. In some embodiments, the procedure device hub is attached to a ceiling such that a user (e.g., a physician) may move it into a desired position (thereby avoiding having to position the energy delivery system utilization sources (e.g., cables, wires, cords, tubes, pipes providing energy, gas, coolant, liquid, pressure, and communication items) on or near a patient while in use). In some embodiments, the procedure device hub is configured to communicate (wirelessly or via wire) with a processor (e.g., a computer, with the Internet, with a cellular phone, with a PDA). In some embodiments, the procedure device hub has thereon one or more lights. In some embodiments, the procedure device hub is configured to compress transported coolants (e.g., $CO_2$) at any desired pressure so as to, for example, retain the coolant at a desired pressure (e.g., the critical point for a gas) so as to improve cooling or temperature maintenance. For example, in some embodiments, a gas is provided at or near its critical point for the purpose of maintaining a temperature of a device, line, cable, or other component at or near a constant, defined temperature. In some such embodiments, a component is not cooled per se, in that its temperature does not drop from a starting temperature (e.g., room temperature), but instead is maintained at a constant temperature that is cooler than where the component would be, but for the intervention. For example, $CO_2$ may be used at or near its critical point (e.g., vapor-liquid critical point) (e.g., 31.1 Celsius at 7.821 kPa) to maintain temperature so that components of the system are sufficiently cool enough not to burn tissue, but likewise are not cooled or maintained significantly below room temperature or body temperature such skin in contact with the component freezes or is otherwise damaged by cold. Using such configurations permits the use of less insulation, as there are not "cold" components that must be shielded from people or from the ambient environment. In some embodiments, the procedure device hub has a retracting element designed to recoil used and/or unused cables, wires, cords, tubes, and pipes providing energy, gas, coolant, liquid, pressure, and/or communication items. In some embodiments, the procedure device hub is configured to prime coolants for distribution into, for example, an energy delivery device such that the coolant is at a desired temperature prior to use of the energy delivery device. In some embodiments, the procedure device hub has therein software configured to prime coolants for distribution into, for example, an energy delivery device such that the system is at a desired temperature prior to use of the energy delivery device. In some embodiments, the use of a procedure device hub permits the use of shorter cables, wires, cords, tubes, and/or pipes (e.g., less than 4 feet, 3 feet, 2 feet). In some embodiments, the procedure device hub and/or one more components connected to it, or portions thereof are covered by a sterile sheath.

In one illustrative embodiment, a import/export box contains one or more microwave power sources and a coolant supply (e.g., pressurized carbon dioxide gas). This import/export box is connected to a single transport sheath that delivers both the microwave energy and coolant to a procedure device hub. The coolant line or the energy line within the transport sheath may be wound around one another to permit maximum cooling of the transport sheath itself. The transport sheath is run into the sterile field where a procedure it to take place along the floor in a location that does not interfere with the movement of the medical team attending to the patient. The transport sheath connects to a table located near an imaging table upon which a patient lays. The table is portable (e.g., on wheels) and connectable to the imaging table so that they move together. The table contains arm, which may be flexible or telescoping, so as to permit positioning of the arm above and over the patient. The transport sheath, or cables connected to the transport sheath, run along the arm to the overhead position. At the end of the arm is the procedure device hub. In some embodiments, two or more arms are provided with two or more procedure device hubs or two or more sub-components of a single procedure device hub. The procedure device hub is small (e.g., less than 1 foot cube, less than 10 cm cube, etc.) to allow easy movement and positioning above the patient. The procedure device hub contains a processor for controlling all computing aspects of the system. The device hub contains one or more connections ports for connecting cables that lead to energy delivery devices. Cables are connected to the ports. The cables are retractable and less than three feet in length. Use of short cables reduces expense and prevents power loss. When not in use, the cables hang in the air above the patient, out of contact with the patient's body. The ports are configured with a dummy load when not in use (e.g., when a energy delivery device is not connected to a particular port). The procedure device hub is within reach of the treating physician so that computer controls can be adjusted and displayed information can be viewed, in real-time, during a procedure.

X. Uses for Energy Delivery Systems

The systems of the present invention are not limited to particular uses. Indeed, the energy delivery systems of the present invention are designed for use in any setting wherein the emission of energy is applicable. Such uses include any and all medical, veterinary, and research applications. In addition, the systems and devices of the present invention may be used in agricultural settings, manufacturing settings, mechanical settings, or any other application where energy is to be delivered.

In some embodiments, the systems are configured for open surgery, percutaneous, intravascular, intracardiac, endoscopic, intraluminal, laparoscopic, or surgical delivery of energy. In some embodiments, the systems are configured for delivery of energy to a target tissue or region. In some embodiments, a positioning plate is provided so as to improve percutaneous, intravascular, intracardiac, laparoscopic, and/or surgical delivery of energy with the energy delivery systems of the present invention. The present invention is not limited to a particular type and/or kind of positioning plate. In some embodiments, the positioning plate is designed to secure one or more energy delivery devices at a desired body region for percutaneous, intravascular, intracardiac, laparoscopic, and/or surgical delivery of energy. In some embodiments, the composition of the positioning plate is such that it is able to prevent exposure of the body region to undesired heat from the energy delivery system. In some embodiments, the plate provides guides for assisted positioning of energy delivery devices. The present invention is not limited by the nature of the target tissue or region. Uses include, but are not limited to, treatment of heart arrhythmia, tumor ablation (benign and malignant), control of bleeding during surgery, after trauma, for any other control of bleeding, removal of soft tissue, tissue resection and harvest, treatment of varicose veins, intraluminal tissue ablation (e.g., to treat esophageal pathologies such as Barrett's Esophagus and esophageal adenocarcinoma), treatment of bony tumors, normal bone, and benign bony conditions, intraocular uses, uses in cosmetic surgery, treatment of pathologies of the central nervous system including brain tumors and electrical disturbances, sterilization procedures (e.g., ablation of the fallopian tubes) and cauterization of blood vessels or tissue for any purposes. In some embodiments, the surgical application comprises ablation therapy (e.g., to achieve coagulative necrosis). In some embodiments, the surgical application comprises tumor ablation to target, for example, metastatic tumors. In some embodiments, the device is configured for movement and positioning, with minimal damage to the tissue or organism, at any desired location, including but not limited to, the brain, neck, chest, abdomen, and pelvis. In some embodiments, the systems are configured for guided delivery, for example, by computerized tomography, ultrasound, magnetic resonance imaging, fluoroscopy, and the like.

In certain embodiments, the present invention provides methods of treating a tissue region, comprising providing a tissue region and a system described herein (e.g., an energy delivery device, and at least one of the following components: a processor, a power supply, a temperature monitor, an imager, a tuning system, and/or a temperature reduction system); positioning a portion of the energy delivery device in the vicinity of the tissue region, and delivering an amount of energy with the device to the tissue region. In some embodiments, the tissue region is a tumor. In some embodiments, the delivering of the energy results in, for example, the ablation of the tissue region and/or thrombosis of a blood vessel, and/or electroporation of a tissue region. In some embodiments, the tissue region is a tumor. In some embodiments, the tissue region comprises one or more of the heart, liver, genitalia, stomach, lung, large intestine, small intestine, brain, neck, bone, kidney, muscle, tendon, blood vessel, prostate, bladder, and spinal cord.

EXPERIMENTAL

Example I

Figure 9:
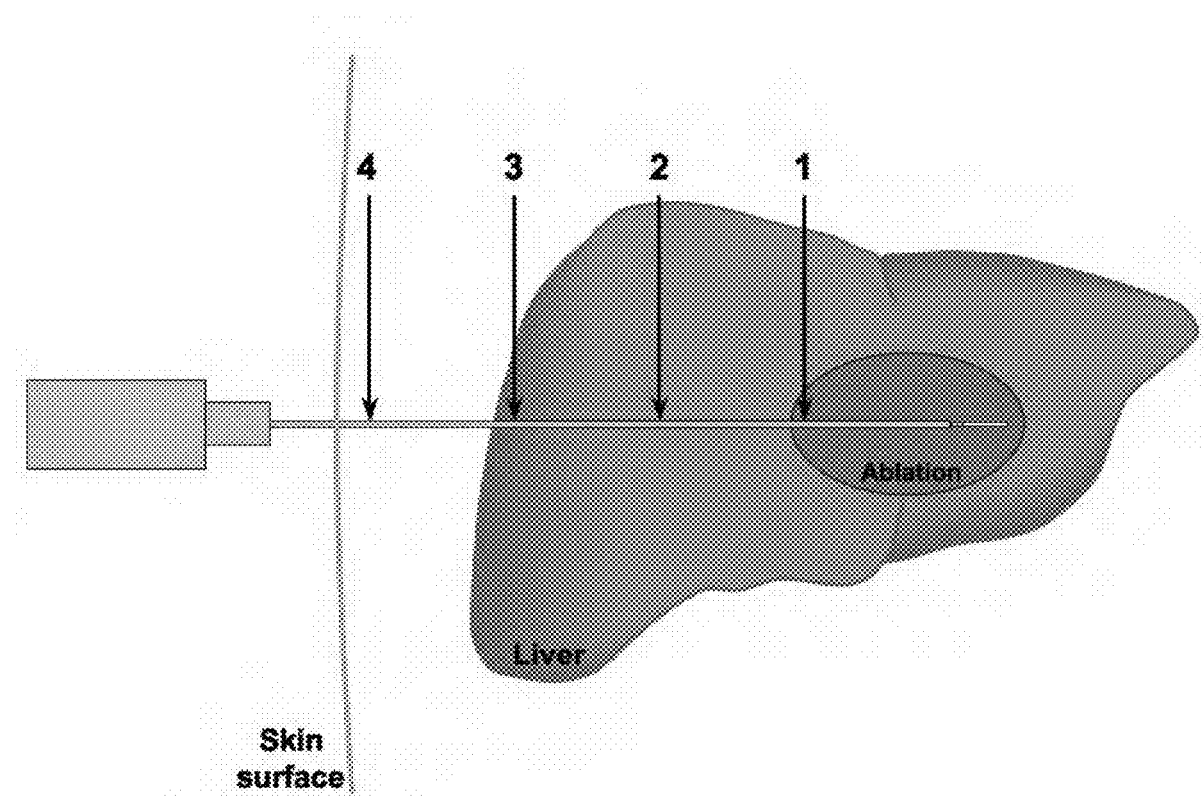
FIG. 9 shows the test setup and position of temperature measurement stations. As shown, the ablation needle shaft for all experiments was 20.5 cm. Probes 1, 2 and 3 were located 4, 8 and 12 cm proximal to the tip of the stainless needle.

This example demonstrates the avoidance of undesired tissue heating through use of an energy delivery device of the present invention circulating coolant through coolant channels. The ablation needle shaft for all experiments was 20.5 cm. There was minimal cooling of the handle assembly indicating that handle-cooling effects were well-isolated. Temperature probes 1, 2 and 3 were located at 4, 8 and 12 cm proximal to the tip of the stainless needle (see FIG. 9). Temperature measurements were taken for 35% power measurement following insertion into a pig liver and 45% power measurement following insertion into a pig liver. For the 35% power measurement, Probe 4 was on the handle itself. For the 45% power measurements, Probe 4 was located at the needle-skin interface, approximately 16 cm back from the stainless needle tip.

Figure 10:
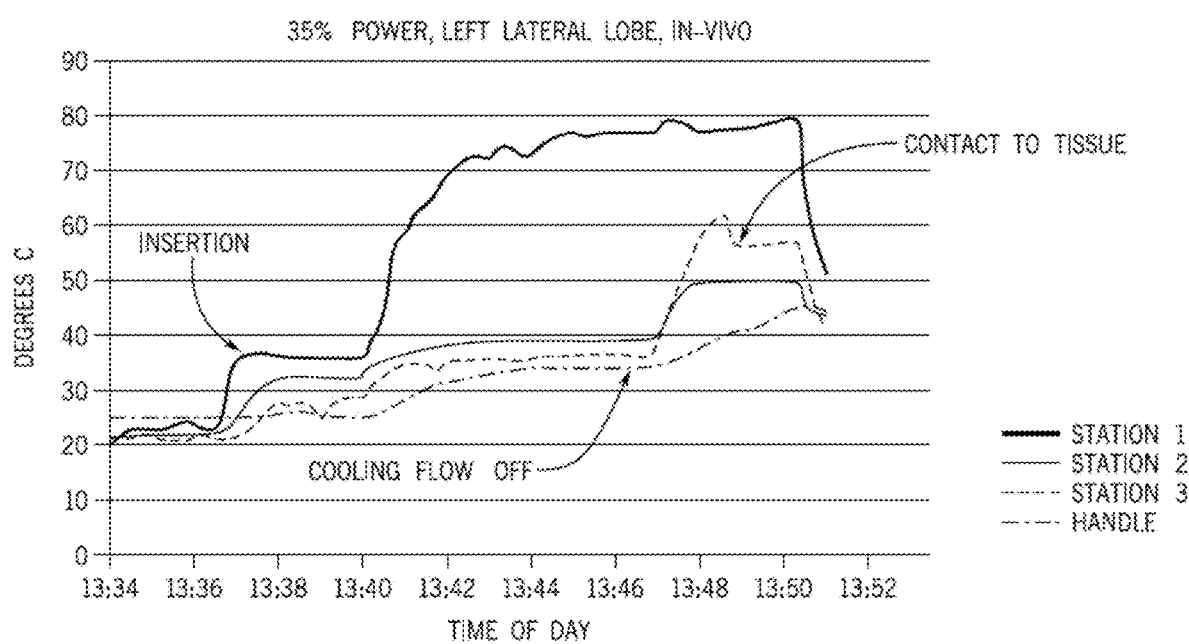
FIG. 10 shows treatment at 35% (microwaves "on" from 13:40 to 13:50) with anomalously high (6.5%) reflected power. Probe 3 was initially placed just outside of the liver tissue, in air.

As shown in FIG. 10, treatment at 35% power for 10 minutes with anonymously high (6.5%) reflected power demonstrated maintenance of the device at a non-tissue damaging temperature at Probes 1, 2, 3 and the handle.

Figure 11:
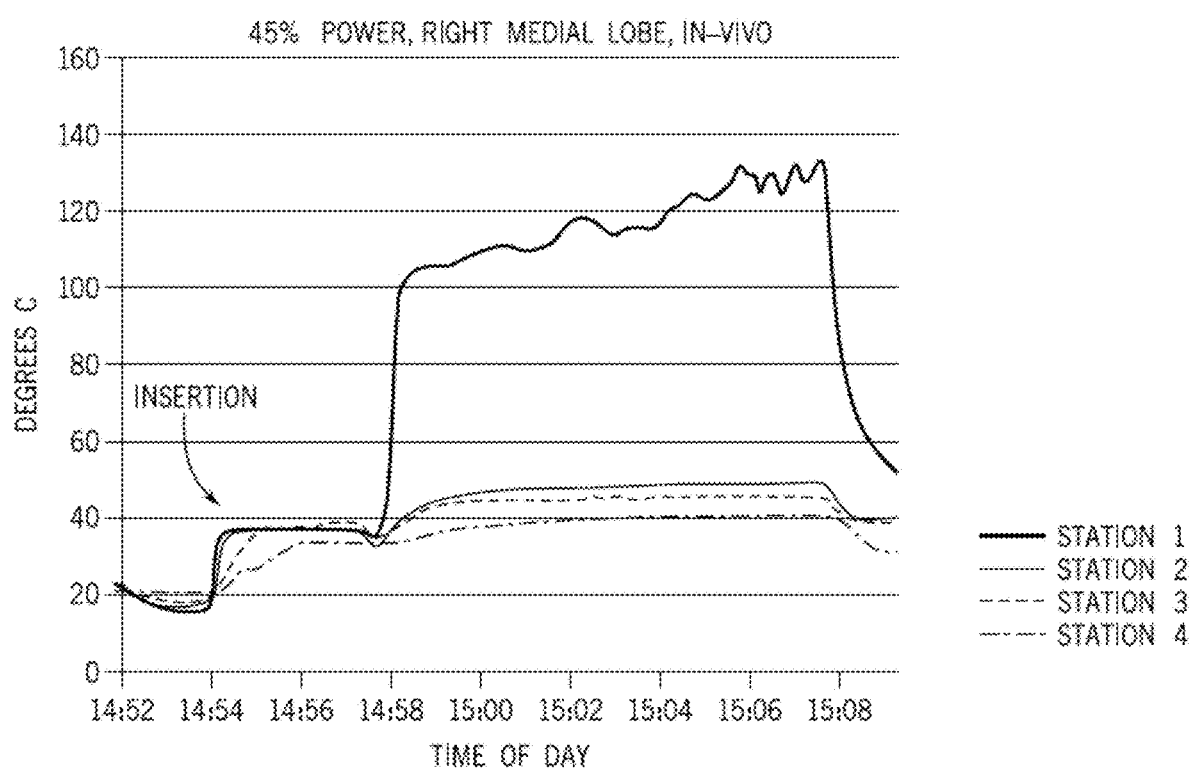
FIG. 11 shows 10 minute treatment at 45% (microwaves on from 14:58 to 15:08) with anomalously high (6.5%) reflected power. Peak temperature at Station 4 was 40.25° C.
Figure 12:
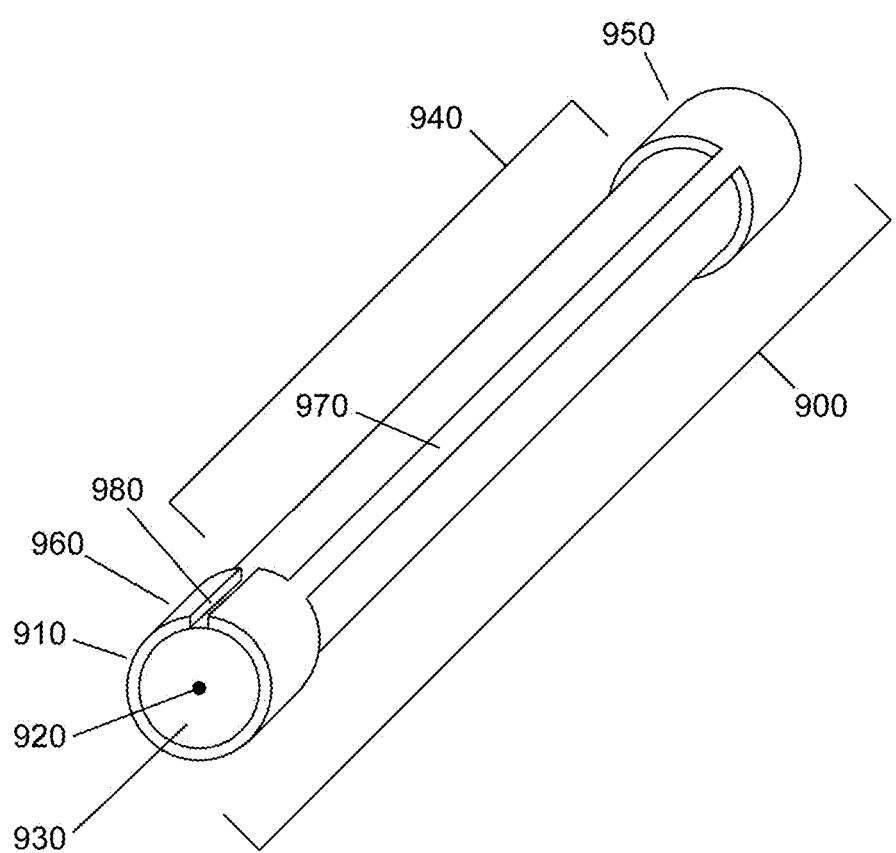
FIG. 12 shows one a coaxial cable having a region of its outer conductor removed to create space for coolant flow in one embodiment of the present invention.

As shown in FIG. 11, treatment at 45% power for 10 minutes with anonymously high (6.5%) reflected power demonstrated maintenance of the device at a non-tissue damaging temperature at Probes 1, 2, 3 and 4. Observation of the skin and fat layers after 10 minutes ablation at 45% power for 10 minutes with anonymously high (6.5%) reflected power demonstrating no visible burns or thermal damage.

Example II

This example demonstrates generator calibration. Generator calibration was done by Cober-Muegge at the factory and was set to be most accurate for powers greater than 150 W. The magnetron behaved much like a diode: increasing cathode voltage did not increase vacuum current (proportional to output power) until a critical threshold was reached, at which point vacuum current increased rapidly with voltage. Control of the magnetron source relied on accurate control of the cathode voltage near that critical point. As such, the generator was not specified for powers from 0-10% and correlation between the output power and theoretical power percentage input was poor below 15%.

To test the generator calibration, the power control dial was changed from 0.25% in 1% increments (corresponding to theoretical output powers of 0-75 W in 3 W increments) and the generator's output power display was recorded and power output measured. The measured power output was adjusted for the measured losses of the coaxial cable, coupler and load at room temperature. The output display was also adjusted for offset error (i.e., the generator read 2.0% when the dial was set to 0.0%).

The error between the dial and generator output power display was large for low-power dial settings. These two values quickly converged to a percent error of less than 5% for dial settings above 15%. Similarly, the measured output power was significantly different from the theoretical output power for dial settings below 15% but more accurate for dial settings above 15%.

Example III

This example describes the setup and testing of an antenna during manufacturing. This provides a method for setup and tested in a manufacturing environment. The method employs a liquid, tissue-equivalent phantom rather than tissue.

From the numerical and experimental measurements already made on the antenna, it was known that changes in L2 of ~1 mm will increase the reflected power from <−30 dB to ~−20-25 dB. This increase was likely made less significant by the changes in tissue properties that occurred during ablation and so we would consider at relative tolerance of 0.5 mm on the length L2 is reasonable. Likewise, a tolerance of 0.5 mm on the length L1 is used, even though the total reflection coefficient depends less on L1 than L2.

Testing of the antenna tuning for quality control purposes can be achieved using a liquid solution designed to mimic the dielectric properties of liver, lung or kidney (see, e.g., Guy A W (1971) IEEE Trans. Microw. Theory Tech. 19:189-217; herein incorporated by reference in its entirety). The antenna is immersed in the phantom and the reflection coefficient recorded using a 1-port measurement device or full vector network analyzer (VNA). Verification of a reflection coefficient below −30 dB is selected to ensure proper tuning.

All publications and patents mentioned in the above specification are herein incorporated by reference. Various modifications and variations of the described method and system of the invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

We claim:

1. A system comprising
two or more energy delivery antennas,
a processor,
a microwave power supply, and
a power splitter electrically connected to the two or more energy delivery antennas and the power supply, wherein the power splitter is configured to provide varying amounts of energy to the two or more energy delivery antennas,
wherein the processor is configured to simultaneously manipulate and/or control the two or more energy delivery antennas, the power splitter, and the microwave power supply,
wherein said processor is configured to
generate a predicted map of a tissue ablation region,
direct placement of the two or more energy delivery antennas during delivery of ablation energy based on the predicted map of the tissue ablation region to achieve a desired ablation result,
readjust the predicted map of the tissue ablation region during the delivery of ablation energy, and
redirect placement of the two or more energy delivery antennas during the delivery of ablation energy based on the readjusted predicted map of the tissue ablation region to achieve the desired ablation result.

2. The system of claim 1, wherein the power slitter is configured to electrically isolate the energy delivered to each of the two or more energy delivery antennas.

3. The system of claim 1, wherein the power splitter is able to connect with one or more additional system components.

4. The system of claim 1, further comprising one or more of the following: a temperature adjustment system, a tuning system, or an imaging system.

5. The system of claim 1, wherein the power splitter is a 2-4 channel power splitter.

6. The system of claim 1, wherein the power splitter is a 1000-watt-rated 2-4 channel power splitter.

7. The system of claim 1, wherein the two or more energy delivery antennas are configured to operate simultaneously.

8. The system of claim 1, wherein the system is configured to phase fields for constructive or destructive interference.

9. A method of ablating a sample, comprising contacting the two or more energy delivery antennas of claim 1 with the sample, and ablating the sample.

10. The method of claim 9, wherein said sample is a tissue sample.

11. The method of claim 10, wherein said tissue sample comprises a tumor.

12. The method of claim 9, wherein the sample is an in vivo sample.

* * * * *